United States Patent
Barlow et al.

(10) Patent No.: US 8,540,621 B2
(45) Date of Patent: Sep. 24, 2013

(54) MEDICAL RETAINER AND MEDICAL OPERATION USING THE SAME

(75) Inventors: David E. Barlow, Coopersburg, PA (US); Takayasu Mikkaichi, Tokyo (JP); Kensei Nakahashi, Tokyo (JP); Hironobu Kawano, Tokyo (JP); Kunihide Kaji, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1113 days.

(21) Appl. No.: 11/652,954

(22) Filed: Jan. 12, 2007

(65) Prior Publication Data

US 2007/0265600 A1    Nov. 15, 2007

Related U.S. Application Data

(63) Continuation-in-part of application No. 11/331,966, filed on Jan. 13, 2006, now Pat. No. 8,002,695.

(60) Provisional application No. 60/771,671, filed on Feb. 9, 2006.

(51) Int. Cl.
   *A61B 1/00* (2006.01)
   *A61B 1/04* (2006.01)
   *A61B 1/12* (2006.01)

(52) U.S. Cl.
   USPC ............................ 600/104; 600/115; 600/158

(58) Field of Classification Search
   USPC .................. 600/104, 115, 116, 158; 604/41, 604/45, 99.03, 101.01, 103, 516
   See application file for complete search history.

(56) References Cited

U.S. PATENT DOCUMENTS

| | | | |
|---|---|---|---|
| 4,180,076 A * | 12/1979 | Betancourt | 604/101.03 |
| 4,445,892 A | 5/1984 | Hussein et al. | |
| 4,598,707 A * | 7/1986 | Agdanowski et al. | 128/207.15 |
| 4,834,725 A * | 5/1989 | Iwatschenko | 604/530 |
| 5,167,627 A | 12/1992 | Clegg et al. | |
| 5,297,536 A | 3/1994 | Wilk | |
| 5,349,950 A * | 9/1994 | Ulrich et al. | 128/207.16 |

(Continued)

FOREIGN PATENT DOCUMENTS

EP    1 151 729 A1   11/2001
JP    S58-73212 U    5/1983

(Continued)

OTHER PUBLICATIONS

U.S. Office Action dated Apr. 12, 2010 received in related U.S. Appl. No. 11/331,966.

(Continued)

*Primary Examiner* — Alireza Nia
(74) *Attorney, Agent, or Firm* — Scully, Scott, Murphy & Presser, P.C.

(57) ABSTRACT

A medical retainer is provided capable of independently controlling supplying air and water to a hollow organ like a stomach and a lumen of a small intestine. The medical retainer for sealing a fluid, the retainer being subject to be retained in a gastrointestinal tract of a patient, the medical retainer includes: a sealing section for sealing the fluid, the sealing section making contact with a wall of the gastrointestinal tract; a main body having passageways; and directional valves disposed in the passageways for allowing one of upward flow and downward flow of the fluid relative to the position of the retainer.

15 Claims, 22 Drawing Sheets

(56) References Cited

U.S. PATENT DOCUMENTS

| | | | |
|---|---|---|---|
| 5,458,131 | A | 10/1995 | Wilk |
| 5,527,280 | A * | 6/1996 | Goelz ................. 604/99.02 |
| 6,027,499 | A | 2/2000 | Johnston et al. |
| 6,238,335 | B1 | 5/2001 | Silverman et al. |
| 6,991,602 | B2 | 1/2006 | Nakazawa et al. |
| 2001/0049497 | A1* | 12/2001 | Kalloo et al. ............ 604/164.01 |
| 2002/0042564 | A1 | 4/2002 | Cooper et al. |
| 2005/0033331 | A1* | 2/2005 | Burnett et al. ................ 606/154 |
| 2005/0222491 | A1 | 10/2005 | Uesugi et al. |
| 2005/0234391 | A1 | 10/2005 | Uesugi et al. |
| 2005/0273060 | A1* | 12/2005 | Levy et al. .................... 604/192 |
| 2006/0229653 | A1 | 10/2006 | Wilk |
| 2006/0241344 | A1 | 10/2006 | Wilk |
| 2006/0241570 | A1 | 10/2006 | Wilk |
| 2007/0123781 | A1 | 5/2007 | Callahan et al. |

FOREIGN PATENT DOCUMENTS

| | | |
|---|---|---|
| JP | 2002-153563 | 5/2002 |
| JP | 2003-506132 | 2/2003 |
| JP | 2005-287839 | 10/2005 |
| JP | 2005-287840 | 10/2005 |
| WO | WO 01/10314 A2 | 2/2001 |

OTHER PUBLICATIONS

Notice of Allowance dated May 9, 2011 of corresponding U.S. Appl. No. 11/331,966.

International Search Report dated Feb. 13, 2007.

Japanese Office Action dated Mar. 6, 2012 from corresponding Japanese Patent Application No. 2007-553935, together with English language translation.

* cited by examiner

MEDICAL RETAINER AND MEDICAL OPERATION USING THE SAME

CROSS-REFERENCE TO RELATED APPLICATION

The present application is a continuation-in-part application of U.S. patent application Ser. No. 11/331,966, filed Jan.13, 2006 now U.S. Pat. No. 8,002,695 and the present application claims priority to U.S. provisional application No. 60/771,671, filed Feb.9, 2006, the contents of which are incorporated herein by reference.

BACKGROUND OF THE INVENTION

1. Field of the Invention

The present invention relates to a medical retainer and, in particular, to a medical retainer capable of independently controlling the supply of air and water to hollow organs such as a stomach and a lumen of a small intestine. Also, the present invention relates to a medical operation using the medical retainer.

2. Description of the Related Art

Laparoscopic instruments are routinely used to perform surgery on organs accessible via the abdominal cavity. In order to perform such surgery, it is necessary to expand the space within the lumen of abdominal cavity to allow for the observation of abdominal organs and the manipulation of laparoscopic surgical instruments. A common method of expanding the lumen of the abdominal cavity is to insufflate this space with pressurized gas. Air, carbon dioxide and nitrous oxide have all been used. The insufflation of gas into the space of the abdominal cavity separates the patient's abdominal wall from the organs beneath it, thus creating a working space between the abdominal wall and the organs within the abdominal cavity.

Transgastric endoscopic procedures are being developed as an alternative endoscopic means of operating within the lumen of the abdominal cavity. With this surgical approach, a flexible endoscope is passed through the patient's mouth and esophagus into the patient's stomach. An incision or opening is then made in the wall of the stomach, through which the endoscope may be passed out of the stomach into the abdominal cavity. Instruments passed through this transgastrically placed endoscope are then able to perform surgery on abdominal organs in a manner similar to laparoscopic instrumentation.

A current problem of transgastric endoscopic procedures is the inability to independently control insufflation of the stomach, the small intestine, and the lumen of the abdominal cavity.

When the endoscopic procedure is first started, it is desirable to insufflate the stomach in order to expand it, to flatten out the folds of the stomach and to create a working space within the stomach. A clear view of the stomach wall and a substantial working space within the stomach is necessary to facilitate the next step, which is to endoscopically incise the wall of the stomach. The purpose of creating an incision in the wall of the stomach is to create an opening that will allow the distal end of the endoscope to pass from the stomach into the abdominal cavity.

Once the endoscope enters the abdominal cavity, it is desirable to contract the stomach and insufflate the abdominal cavity. Insufflating the abdominal cavity creates a large working space for the flexible endoscope to observe and perform surgery on the abdominal organs. After entering the lumen of the abdominal cavity, it is advantageous to remove the excess gas previously added to the stomach in order to reduce the size of the stomach, and thereby reduce its protrusion into the lumen of the abdominal cavity. In addition, since the stomach communicates with the small intestine via the pylorus, pressurized gas within the stomach will flow into the small intestine, pressurizing the intestines as well. The gas flowing into the small intestine will expand the intestines, causing them to project into the abdominal cavity, further reducing the available working space within the abdominal cavity.

SUMMARY OF THE INVENTION

It is an object of the present invention to use a balloon device placed within the lumen of the proximal small intestine to prevent gas from flowing into and inflating the small intestine during transgastric endoscopic procedures. It is a further object of the present invention to provide a means of removing gas from the distal end of the balloon-obstructed small intestine to further lower its inflated state. It is a further objective of the present invention to provide detachable catheters to this balloon device so that once the balloon is inflated and the small intestine decompressed, the device can be anchored to the wall of the GI tract and the tubes connected to the device can be removed from the patient.

Another object of the present invention is to provide a method that enables easier confirmation of a specific site on a hollow organ, by using an observation device that has been guided into the hollow organ. The present invention further provides a device for this method.

A first aspect of the present invention provides a medical retainer for sealing a fluid so that the retainer is subject to be retained in a gastrointestinal tract of a patient. The medical retainer comprises: a sealing section for sealing the fluid, the sealing section making contact with a wall of the gastrointestinal tract; a main body having passageways; and directional valves disposed in the passageways for allowing one of upward flow and downward flow of the fluid relative to the position of the retainer.

A second aspect of the present invention provides a medical operation via a natural orifice. The method includes: adjusting the patient's body position so that a target site on the anterior wall of the hollow organ faces in the direction opposite to the direction of gravitational force; introducing a liquid inflow conduit in the vicinity of the target site, flowing liquid into the hollow organ via the liquid inflow conduit, to form a liquid holding area and a gas retaining area inside the hollow organ; introducing an observation device into the hollow organ, and confirming the position of the target site from the position of the gas retaining area; and incising while observation the target area.

A third aspect of the present invention provides a medical operation via a natural orifice. The procedure includes: adjusting the patient's body position so that the target site on the anterior wall of the hollow organ faces in the direction opposite to the direction of gravitational force; introducing a liquid inflow conduit in the vicinity of the target site via a natural orifice; flowing a liquid into the hollow organ via the liquid inflow conduit, to form a liquid holding area and a gas retaining area inside the hollow organ; confirming the position of the gas retaining area by using an observation device introduced into the hollow organ via the natural orifice, and confirming the target site based on the position of the gas retaining area; and performing a procedure at the target site while observation the target site.

DETAILED DESCRIPTION OF THE INVENTION

Embodiments will be hereafter explained in detail. In the following description, the same reference symbols are used for the same components, and duplicate description is omitted.

Figure 1:
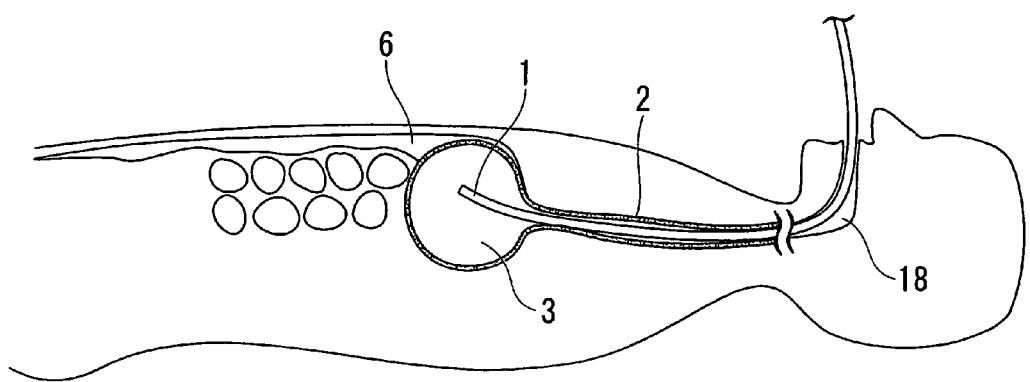
FIG. 1 illustrates an endoscope passing through the mouth and esophagus into the stomach in a side-sectional schematic view of the human torso.
Figure 2:
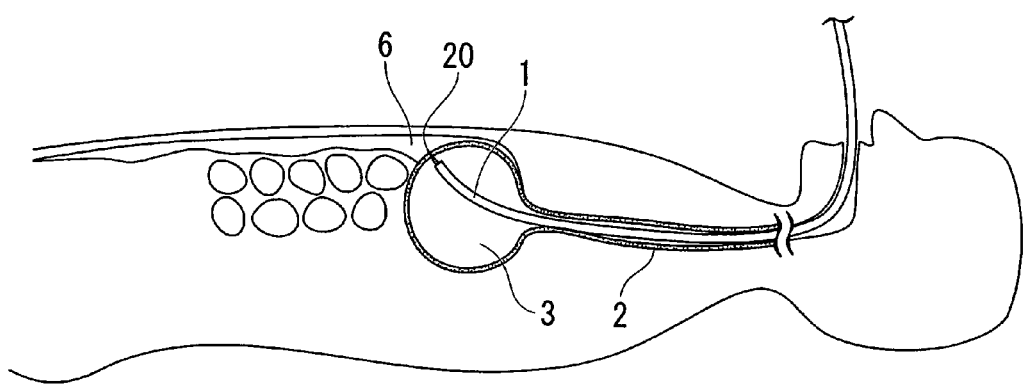
FIG. 2 is a side-sectional schematic view of the human torso illustrating an endoscope employing a needle electrode at its distal tip to make an incision in the wall of the stomach.

FIG. 1 illustrates a flexible endoscope 1 passed through the patient's oropharynx 18 and esophagus 2 and into the stomach 3. Once in the stomach, the endoscope is used to create an incision in the wall of the stomach in order to gain entrance into the lumen 6 of the abdominal cavity. FIG. 2 illustrates that one method of incising the stomach is to use a needle electrode 20 passed through the endoscope 1 to cut an opening in the stomach wall using RF (radio frequency) electrosurgical current. This opening will allow the endoscope to enter the abdominal cavity 6.

Figure 3:
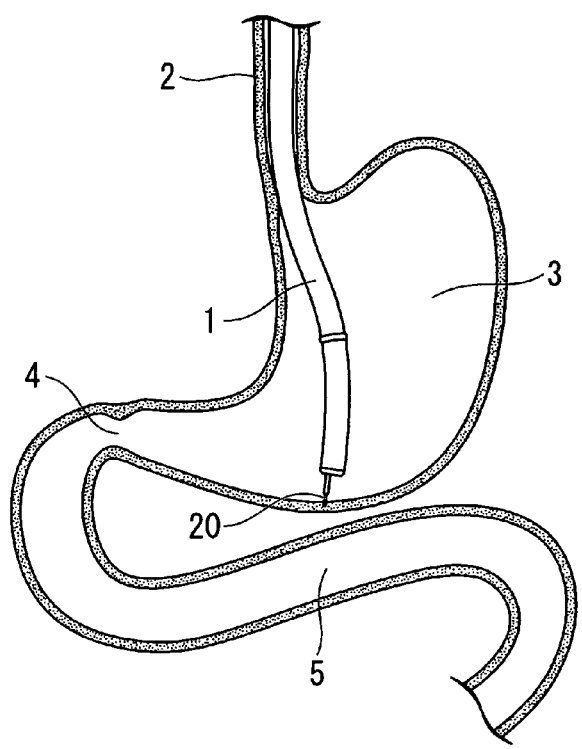
FIG. 3 is an anterior sectional schematic view of the human lower esophagus, stomach and small intestine in the vicinity thereof. An endoscope passed into the stomach with a needle-tipped electrode is being used to create an incision in the wall of the stomach.

FIG. 3 illustrates the same procedure from another point of view, namely looking at the esophagus, stomach and proximal small intestine from an anterior view of the patient. A needle electrode 20 exiting from the tip of the endoscope 1 is being used to create an incision in the wall of the stomach 3. During this procedure it is typical for the endoscopist to inject gas or air through the endoscope into the stomach to expand the stomach for ease of observation and manipulation of the endoscope and endoscopic therapy device. It should be noted however, that the air within the stomach 3 is able to flow through the pylorus 4 and into the proximal small intestine 5, thereby expanding the intestines as well as the stomach.

Figure 4:
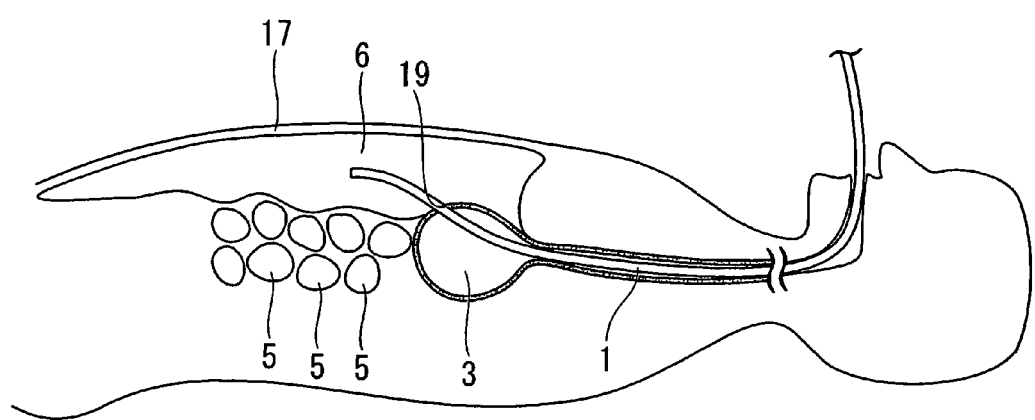
FIG. 4 is a side-sectional schematic view of the human torso with an endoscope passing through an incision in the wall of the stomach and entering the abdominal cavity.

As FIG. 4 illustrates, once an incision 19 is made in the stomach wall, the endoscope 1 is passed into the lumen 6 of the abdominal cavity. By injecting gas through the endoscope, gas can be added to the abdominal cavity raising the abdominal wall 17 from the underlying organs, thereby creating a large working space for the endoscope.

Figure 5:
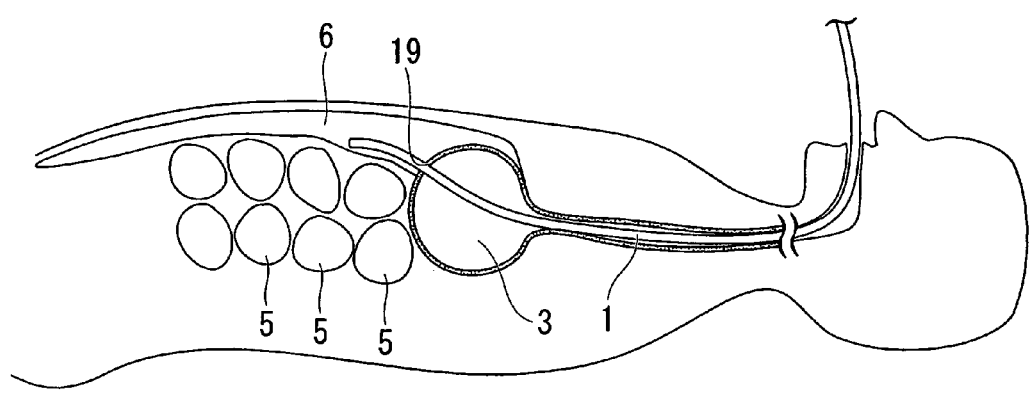
FIG. 5 is a side-sectional schematic view of the human torso with an endoscope passing through an incision in the wall of the stomach and entering the abdominal cavity. As compared with FIG. 4, this figure illustrates that expansion of the stomach and small intestines reduces the size of the lumen of the abdominal cavity.

However, as FIG. 5 illustrates, the size of the lumen 6 of the abdominal cavity will be greatly reduced if the stomach 3 and intestines 5 are also filled with gas. When these organs are filled with gas they expand, impinging on the available space within the lumen of the abdominal cavity, thereby reducing the available working space for manipulating the endoscope and for performing surgery on the abdominal organs.

It is an objective of the present invention to describe a balloon device that can be placed in the pylorus or proximal small intestine to obstruct the passage of gas from the stomach into the small intestine, and thereby allow the small intestine to remain decompressed as the stomach is filled with gas. It is another object of the present invention to provide a means of suctioning the gas that is trapped within the intestines after the balloon is inflated in order to remove this gas, reduce the size of the intestines, and thereby reduce their protrusion into the lumen of the abdominal cavity. It is a further objective of the present invention to allow detachment of the catheter of the balloon to prevent the balloon's catheter from occupying space within the patient's esophagus. It is another object of the present invention to temporarily attach the balloon to the wall of the stomach or pylorus to prevent it from migrating or moving out of position after its placement. Reference numeral 19 shown in FIGS. 4 and 5 indicates an opening formed in the wall of the stomach.

Figure 6A:
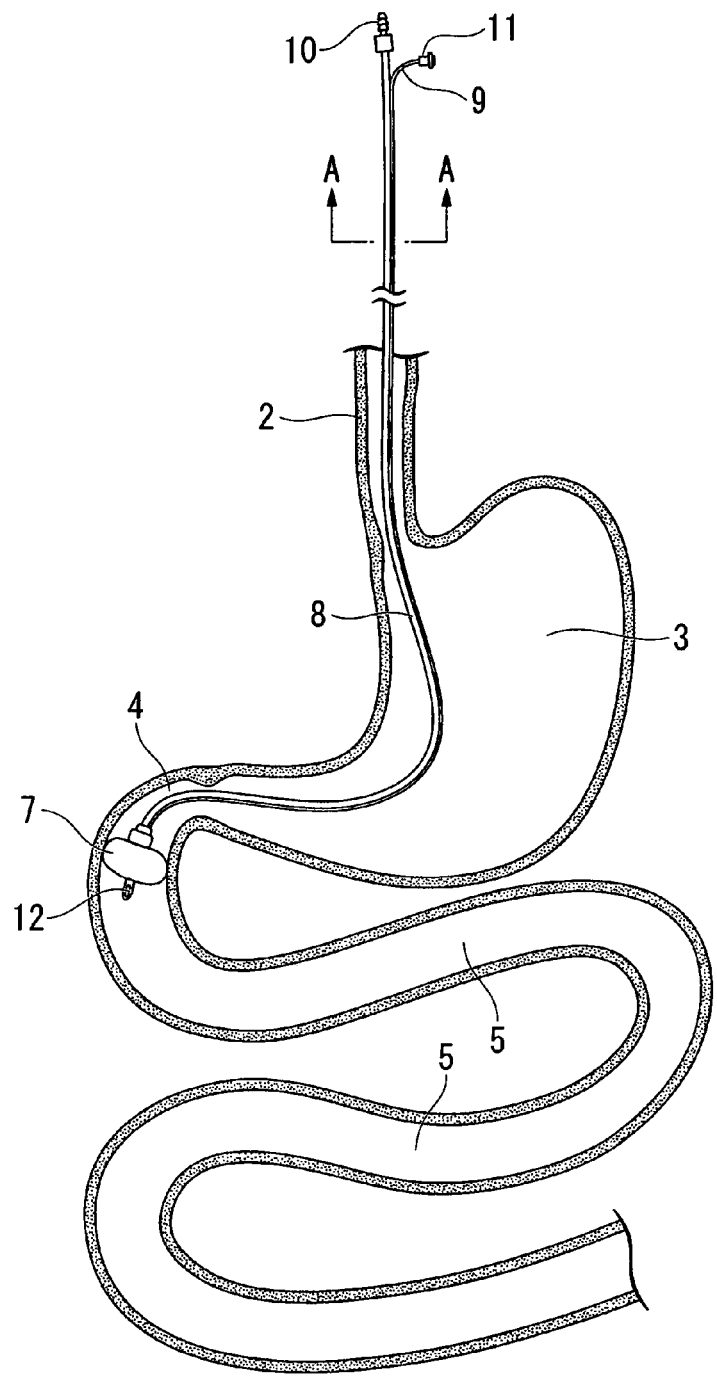
FIG. 6A is an isometric view of a first embodiment of the present invention. The balloon is disposed beyond the pylorus in the proximal small intestine. The proximal end of the catheter and the balloon inflation tube are disposed in the exterior of the patient.

FIG. 6A illustrates an embodiment of the gas-control balloon of the present invention. The balloon 7 is mounted on the tip of a catheter 8 that is long enough to be inserted into the patient through the mouth, esophagus 2 and stomach 3 and into or beyond the pylorus 4. The balloon and catheter are inserted into position with the balloon deflated using traditional means for inserting medical balloon-tipped catheters. Upon placement of the balloon 7 near or past the pylorus 4, the balloon is inflated by injecting gas into the balloon inflation connector 11. When the balloon is expanded so that the surface of the balloon is in full contact with the wall of the pylorus and/or intestine, it will obstruct the further flow of gas from the stomach 3 into the small intestine 5, and vice versa.

When the balloon is thus positioned and inflated, it is possible to apply suction to the catheter by connecting a syringe or pump to the proximal catheter connector 10. This will withdraw gas from the small intestine 5 through the catheter opening 12 distal to the balloon. Removing gas from the small intestine will reduce its size and increase the available space within the abdominal cavity.

Figure 6B:
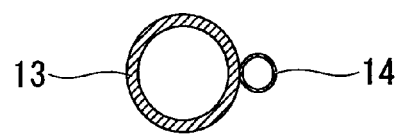
FIG. 6B illustrates a sectional view of the catheter and balloon inflation tube as taken along line A-A in FIG. 6.

FIG. 6B is a cross-section of the catheter illustrated in FIG. 6A through line A-A. It illustrates that the catheter has a first lumen 13 for suctioning gas from the catheter opening (12 in FIG. 6) and a second lumen 14 for inflating/deflating the balloon 7 on the distal end of the catheter.

Figure 7A:
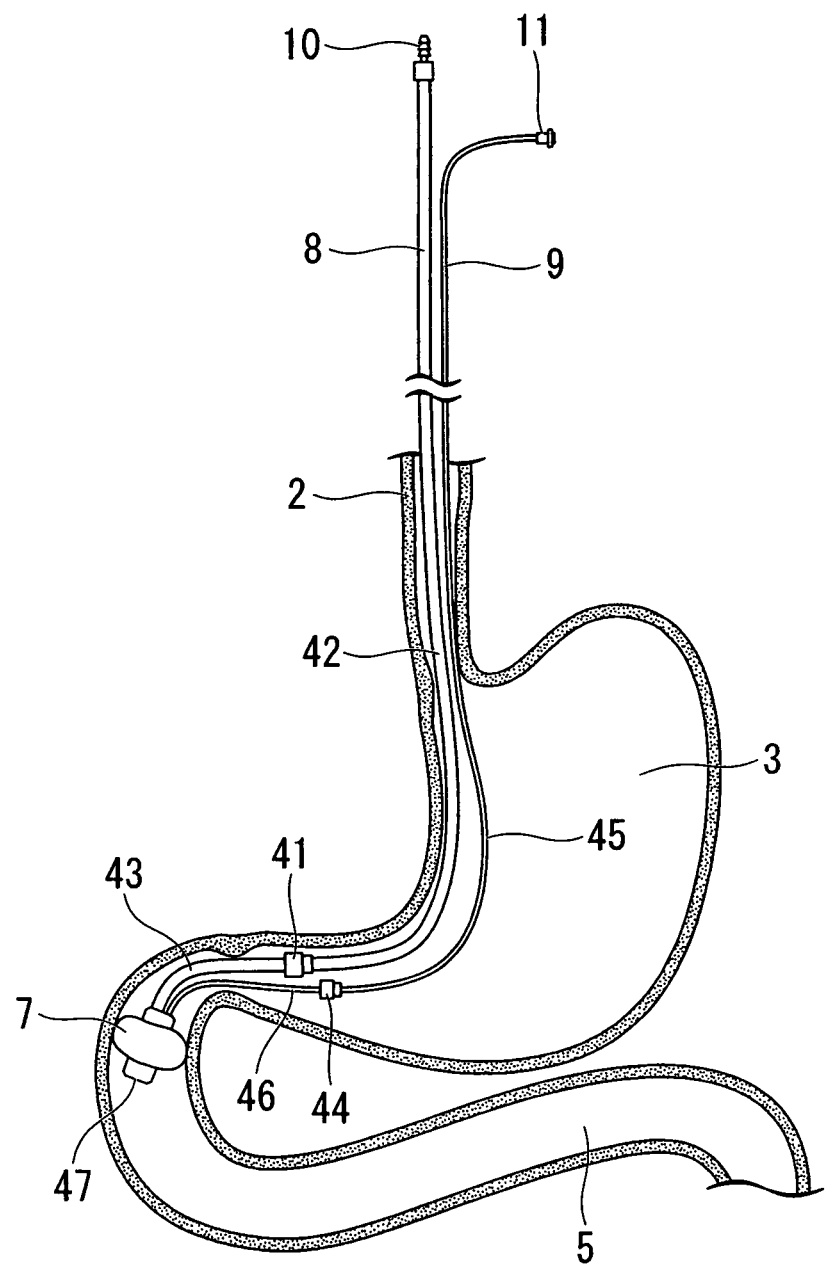
FIG. 7A is an isometric view of a second embodiment of the present invention. The balloon is disposed beyond the pylorus in the proximal small intestine. The proximal end of the catheter and the balloon inflation tube are disposed in the exterior of the patient.
Figure 7B:
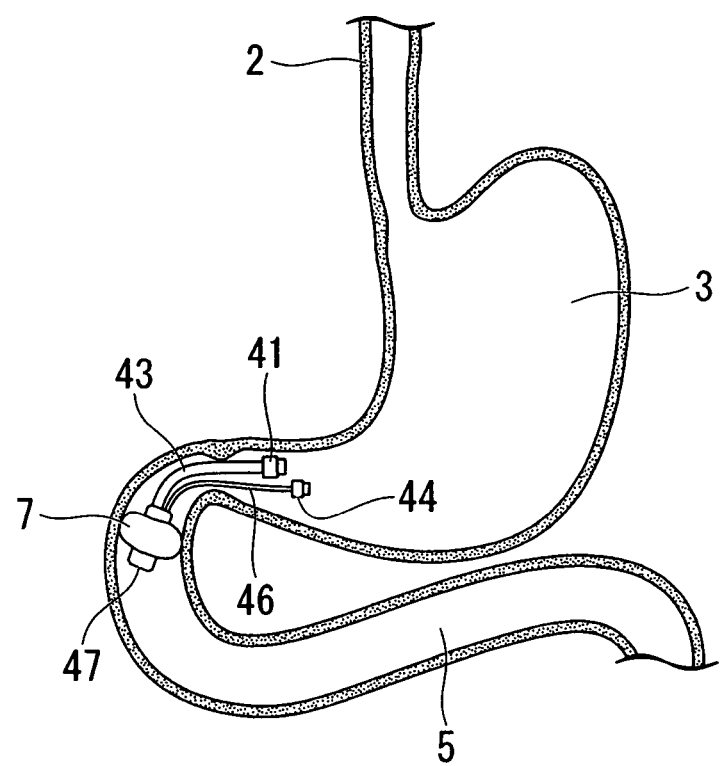
FIG. 7B is a view of the second embodiment of the device after detaching and removing the proximal portions of the catheter and balloon inflation tube.

FIG. 7A illustrates a second embodiment of the present invention. In the present embodiment, the catheter 8 is detachable from the balloon tip 7. The catheter is initially placed and the balloon is inflated near or beyond the pylorus in a manner similar to the first embodiment illustrated in FIG. 6A. After the catheter is placed, gas is withdrawn from the small intestine 5 by applying suction to the catheter connector 10. This will decompress the small intestine, thereby reducing its size.

Once the small intestine has been decompressed it is beneficial to have the capability of removing the catheter from the balloon. The advantage of removing the catheter is that this will leave the stomach and esophagus free for the passage of endoscopes and other devices.

A one-way valve and detachable connector 41 are disposed in the catheter between its distal end 43 and proximal portion 42. The one-way valve allows gas to flow through the catheter only in the direction from a central lumen (not shown) in the catheter hub 47 to the catheter connector 10. This allows decompression of the small intestine 5. The detachable connector 41 allows the proximal part 42 the catheter to be separated from the distal part 43 of the catheter. Likewise, a valve and detachable connector 44 are incorporated in the balloon inflation tube 9 between the distal part of the tube 46 and a more proximal part of the tube 45. This detachable connector 44 allows the proximal part of the inflation tube 45 to be separated from the distal part 46 of the tube connected to the balloon 7. When these two tubes are disconnected, the valve in the detachable connector 44 prevents gas from escaping from the distal inflation tube 46, thereby preventing deflation of the balloon 7.

After positioning the balloon at or beyond the pylorus, the balloon 7 is inflated. Then suction is applied to the catheter connector 10 to decompress the small intestine. At this point, the two tubes connected to the balloon device can be disconnected and removed from the patient. The resulting configuration is illustrated in FIG. 7A.

In this condition, gas in the stomach is prevented by the balloon obstructing the pylorus, and by the one-way valve 41 obstructing flow through the central lumen in the balloon hub 47 from entering the small intestine. The stomach can thus be reinflated without reinflating the small intestine.

Figure 8:
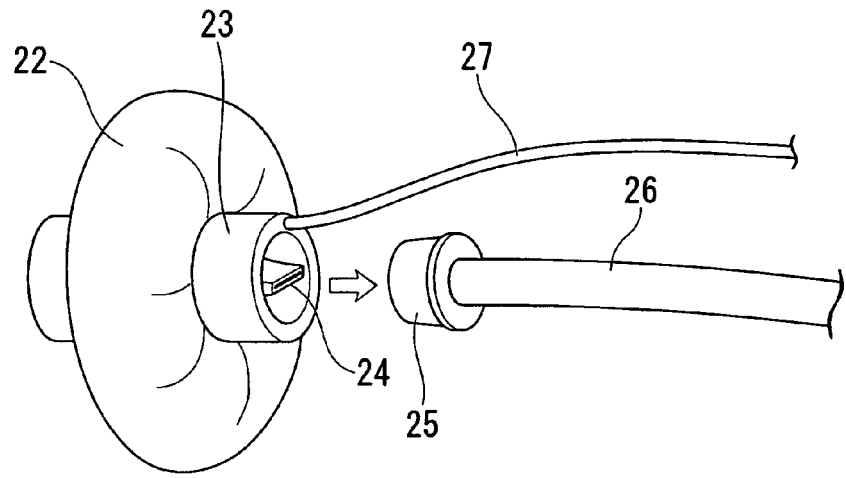
FIG. 8 is an isometric view of a third embodiment of the present invention. The catheter has been disconnected from the balloon hub. A one-way valve is incorporated into the balloon hub.
Figure 9:
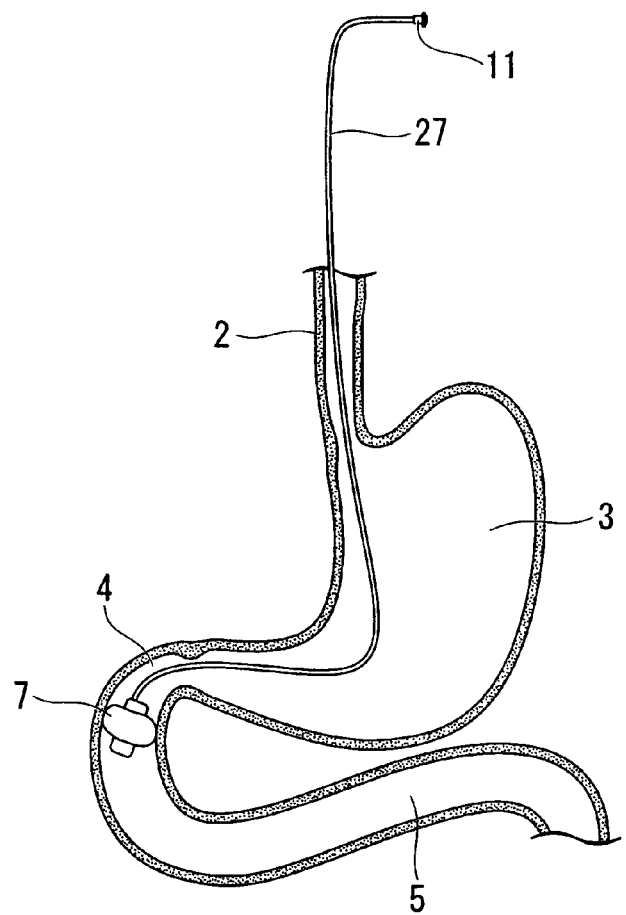
FIG. 9 is a schematic view of the third embodiment of the device illustrating that the balloon is disposed in the patient's small intestine and the balloon inflation tube extends up the esophagus and out of the patient. The catheter has been disconnected from the balloon hub.

FIG. 8 illustrates an embodiment of the invention in which the detachable connection and one-way valve have been incorporated into the balloon hub itself. The embodiment shown in FIG. 8 has a balloon 22 that is inflated by means of an inflation tube 27. A suction catheter 26 connects to the balloon hub 23 via a detachable connector 25. A one-way valve 24 incorporated into the balloon hub 23 allows the flow of gas through a central lumen (not shown) within the hub into the suction catheter 26, but not in the reverse direction. After the balloon catheter has been placed in the pylorus and inflated, gas can be withdrawn from the small intestine by applying suction to the suction catheter. After the small intestine is decompressed, a tug on the suction catheter will detach it from the balloon hub, allowing the catheter to be withdrawn from the patient while leaving the balloon in place in the pylorus. The one-way valve 24 in the hub prevents gas in the stomach from flowing through the lumen in the hub and reinflating the small intestine. As FIG. 9 illustrates, after removing the suction catheter (26 in FIG. 8) the thin balloon inflation tube 27 remains in the patient's esophagus allowing subsequent deflation of the balloon and removal of the device from the patient.

Figure 10:
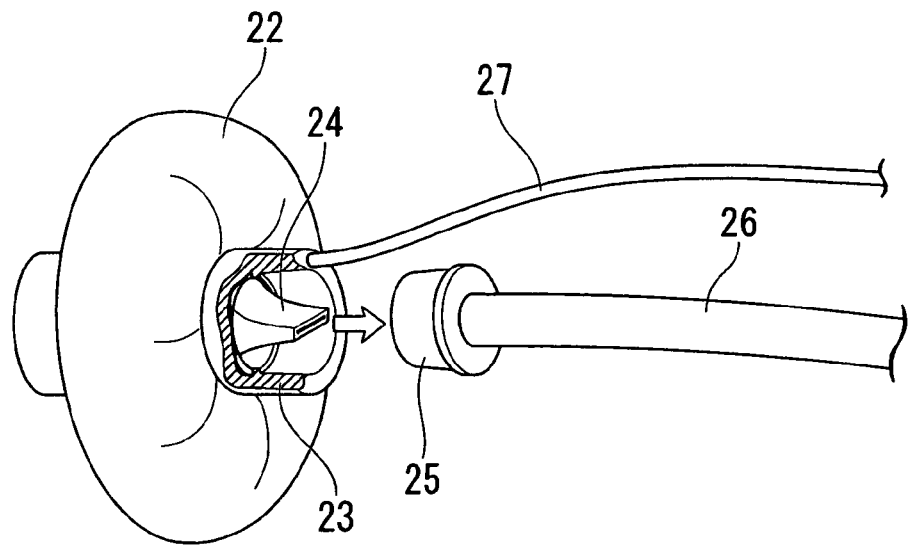
FIG. 10 is an isometric view of the same embodiment as illustrated in FIG. 8. In this illustration a portion of the balloon hub has been cut away for a more complete view of the one-way valve incorporated into the hub.

FIG. 10 shows a cut-away view of the hub 23 providing a clearer view of the one-way valve 24 in the device.

Figure 11:
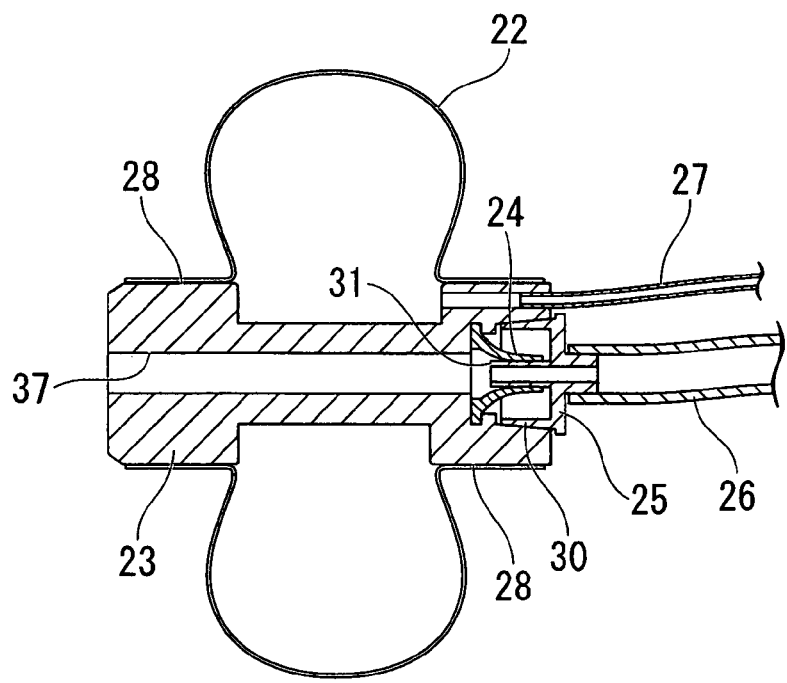
FIG. 11 is a side-sectional view of the balloon and balloon hub of the third embodiment of the device. In this illustration the catheter is attached to the hub.
Figure 12:
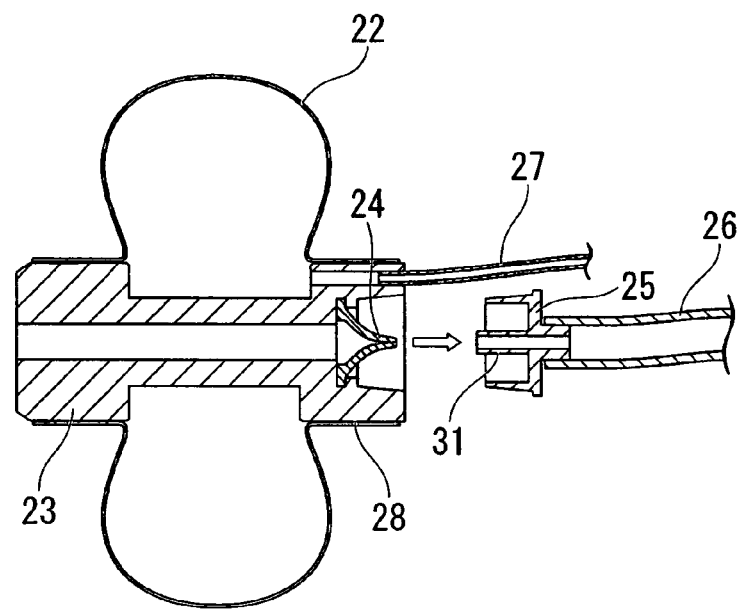
FIG. 12 is a side-sectional view of the balloon and balloon hub of the third embodiment. In this illustration the catheter has been detached from the hub.

FIG. 11 is a cross-sectional view of the embodiment illustrated in FIG. 8 prior to detaching the suction catheter from the hub. The expandable balloon 22 is attached to the hub 23 via adhesive 28, thread wrapping, or other means of attachment. Inflation and deflation of the balloon is achieved by injecting or removing gas, respectively, via the balloon inflation tube 27. Removal of gas distal to the device is achieving by suctioning gas through the central lumen 37 in the hub and then up the lumen of the suction catheter 26. A one-way valve 24 incorporated into the hub is held in an open position by a tubular protruding part 31 on the detachable connector 25 which connects the suction catheter 26 to the balloon hub 23. When in this condition there is a free flow of gas through the device. A tapered friction fit between the mating surfaces 30 of the detachable connector 25 and the hub 23 keeps these two pieces together. However, as FIG. 12 illustrates, a slight tug on the suction catheter 26 will detach the detachable connector 25 from the hub 23. When this happens, the one-way valve 24 incorporated into the hub automatically closes. This valve will allow gas to flow only in the direction of the arrow—that is, from the small intestine into the stomach, not vice versa.

Figure 13:
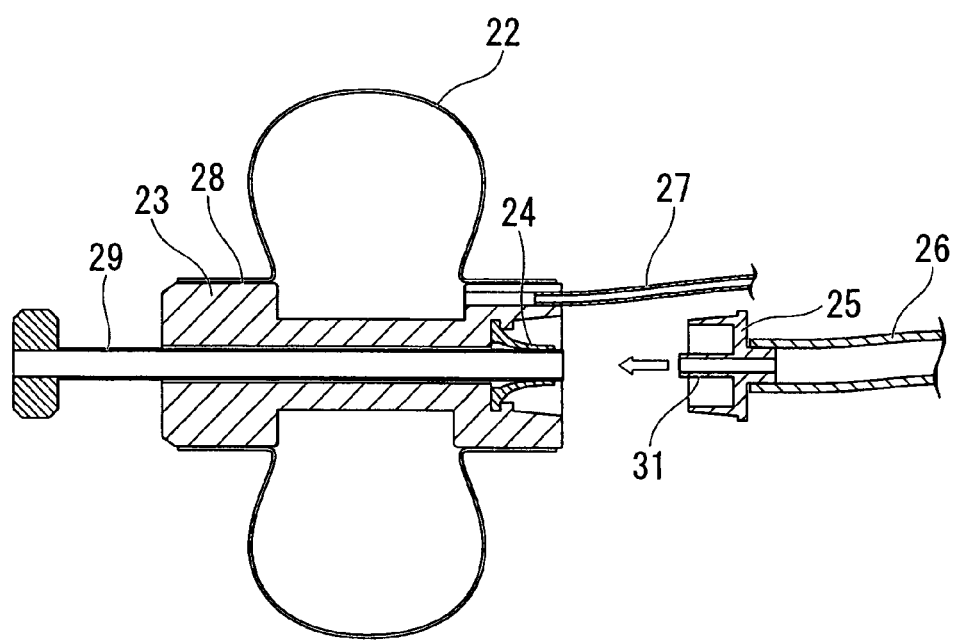
FIG. 13 is a side-sectional view of the balloon and balloon hub of the third embodiment. This illustration shows a means for reattaching the catheter to the hub.

FIG. 13 illustrates how the parts of the device are assembled prior to placing them into the patient. A valve opening tube 29 is first inserted through the central lumen of the hub 23. This tube opens the one-way valve 24 allowing the tubular protruding part 31 of the detachable connector 25 to pass through the one-way valve 24. The pieces are brought together until the mating surfaces of the hub and the detachable connector engage with a friction fit to hold the two pieces together. Once assembled, the valve opening tube 29 is removed and the device is assembled and is in the condition illustrated in FIG. 11.

Figure 14:
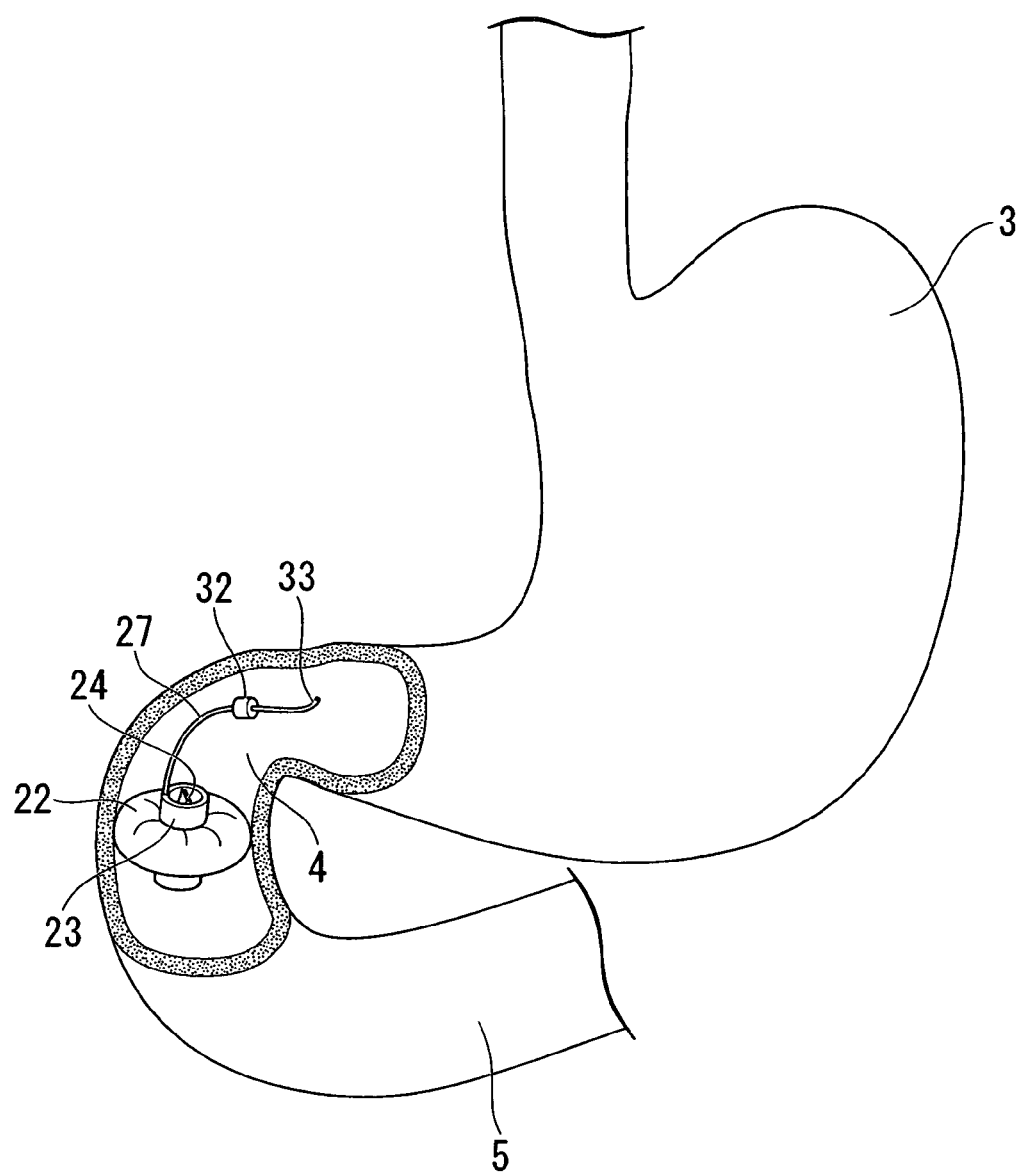
FIG. 14 is an isometric schematic view of a fourth embodiment of the present invention. In this anterior view of the stomach and proximal small intestine, a portion of the tissue has been cut away to illustrate the position of the device within the proximal small intestine. The catheter has been detached. The balloon inflation tube has been endoscopically cut near the one-way valve.

FIG. 14 illustrates an alternative embodiment of the present invention. In this embodiment a one-way valve 32 has also been incorporated into the balloon inflation tube 27. After placing the balloon device at or beyond the pylorus 4, the balloon 22 is inflated and the suction catheter is detached. The one-way valve 24 in the balloon hub allows gas in the small intestine 5 to flow through the device into the stomach 3, but prevents gas from flowing from the stomach into the small intestine. Once the balloon has been inflated to the proper size, endoscopic scissors or other endoscopically employed cutting devices are used to cut the thin balloon inflation tube 27 at a point proximal 33 to the one-way valve 32 in the inflation tube. Since the one-way valve 32 allows air to be supplied to the balloon and prevents the air from flowing out of the balloon, the gas will never flow from the stomach to the small intestine. After the procedure is completed, an endoscopic needle can be used to puncture the balloon and the balloon device is endoscopically removed from the patient.

Figure 15:
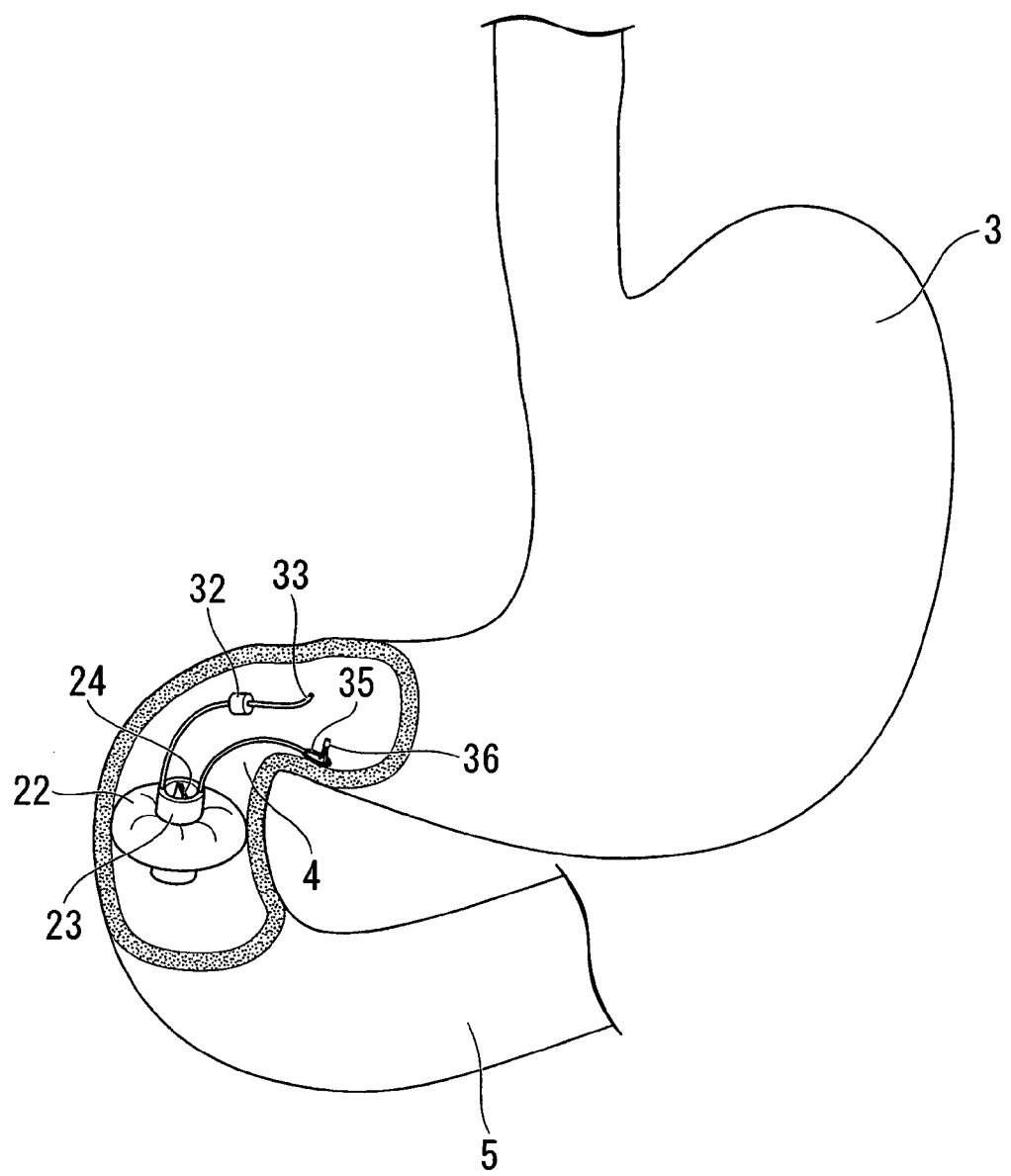
FIG. 15 is an isometric schematic view of a fifth embodiment of the present invention. This embodiment has a fixation loop by which the balloon hub can be anchored in place by means of an endoscopically placed tissue clip.

FIG. 15 illustrates a further modification to the embodiment illustrated in FIG. 14. In this embodiment a fixation loop 35 is firmly attached to the balloon hub 23. Once the balloon is correctly positioned, the fixation loop is temporarily attached to the mucosal surface of the stomach or pylorus by means of an endoscopically applied clip 36 or suture. This temporarily anchors the balloon device and prevents it from migrating further into the small intestine 5. When the procedure is completed, the clip or suture is removed, allowing removal of the balloon device from the patient.

Figure 16:
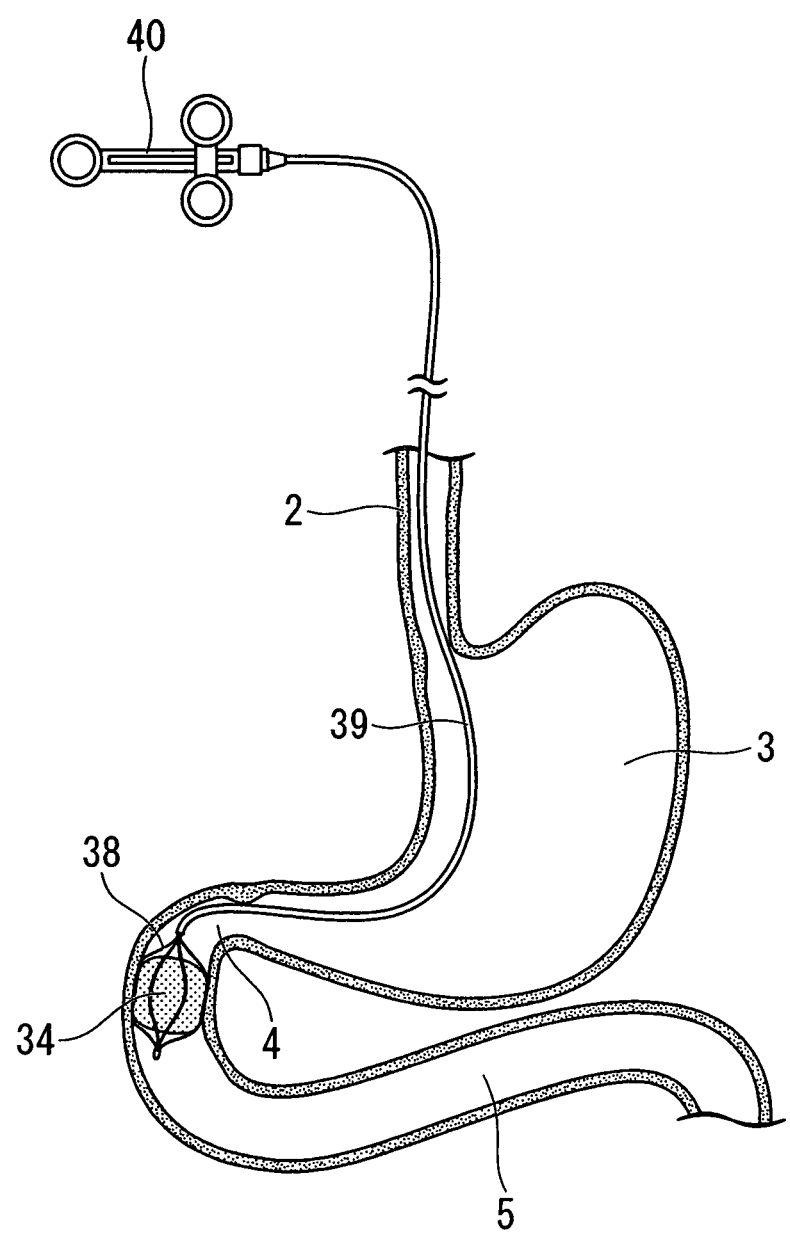
FIG. 16 is an isometric schematic view of a sixth embodiment of the present invention. In this embodiment the lumen of the proximal small intestine is obstructed by a self-expanding closed-cell foam plug. The plug is contained in a wire basket, the handle of which extends outside the patient.

FIG. 16 illustrates a further alternative embodiment of the present invention. In this embodiment a plug of closed-cell foam 34 is constructed of a size and shape that will obstruct gas flow between the stomach 3 and the small intestine 5. The foam plug is loosely held in a thin wire basket 38 attached to the end of a control catheter 39. A handle 40 at the proximal end of the control catheter allows the operator to open and close the basket at will. When the basket is opened (expanded) as shown in FIG. 16, the self-expanding foam plug automatically expands to touch the walls of the intestine and obstruct gas flow between the stomach and the intestines. The closed-cell construction of the foam prevents gas from flowing through the foam plug. The thin catheter 39 attached to the basket remains in the patient during the procedure, preventing migration of the plug and enabling its removal.

Figure 17:
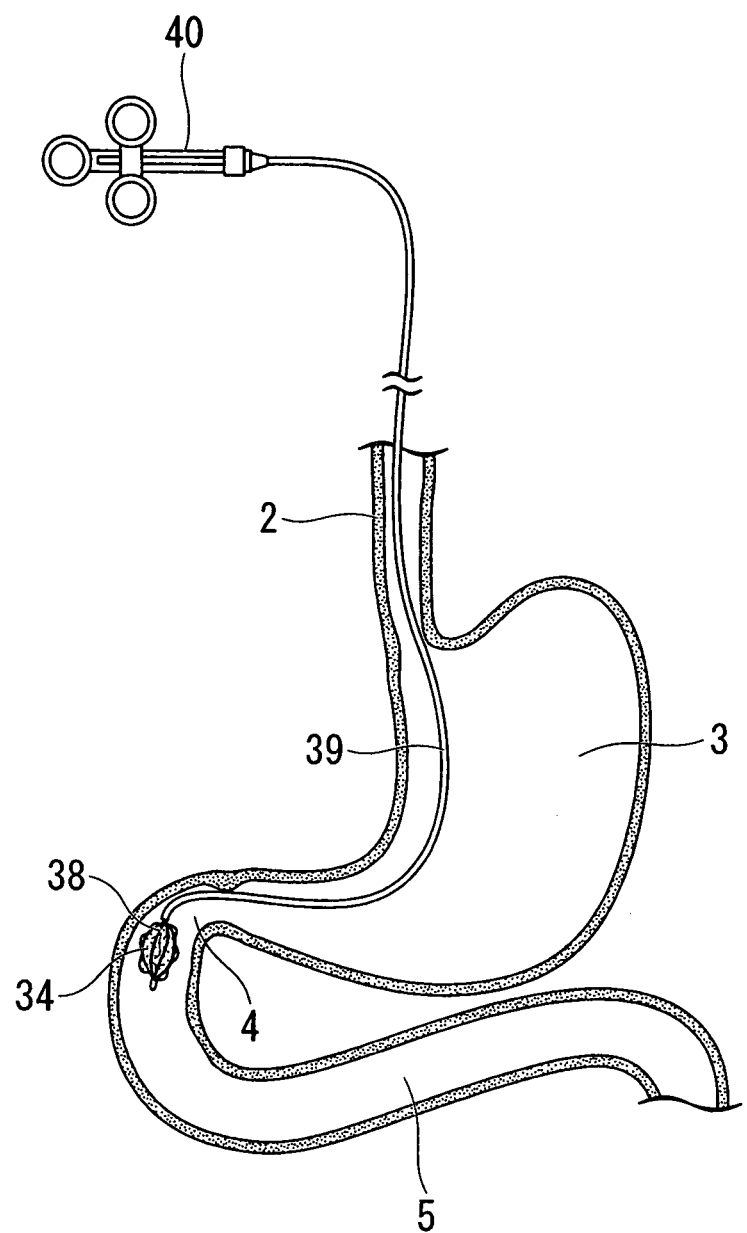
FIG. 17 illustrates the device shown in FIG. 16, but with the basket tightened and compressing the foam plug to reduce its size. In this configuration the device can be easily inserted into or withdrawn from the patient.

FIG. 17 illustrates how the device shown in FIG. 16 is inserted and removed. Operating the handle 40 at the proximal end of the control catheter 39 closes the wire basket 38 holding the foam plug 34 thereby compressing the plug and greatly reducing its size. When the plug compressed it can be easily inserted or withdrawn from the patient.

Embodiments according to the present invention will now be explained in detail below. Structural elements that are equivalent in the following discussion will be assigned the same numeric symbol and redundant explanation thereof will be omitted.

[Seventh Embodiment]

Figure 18:
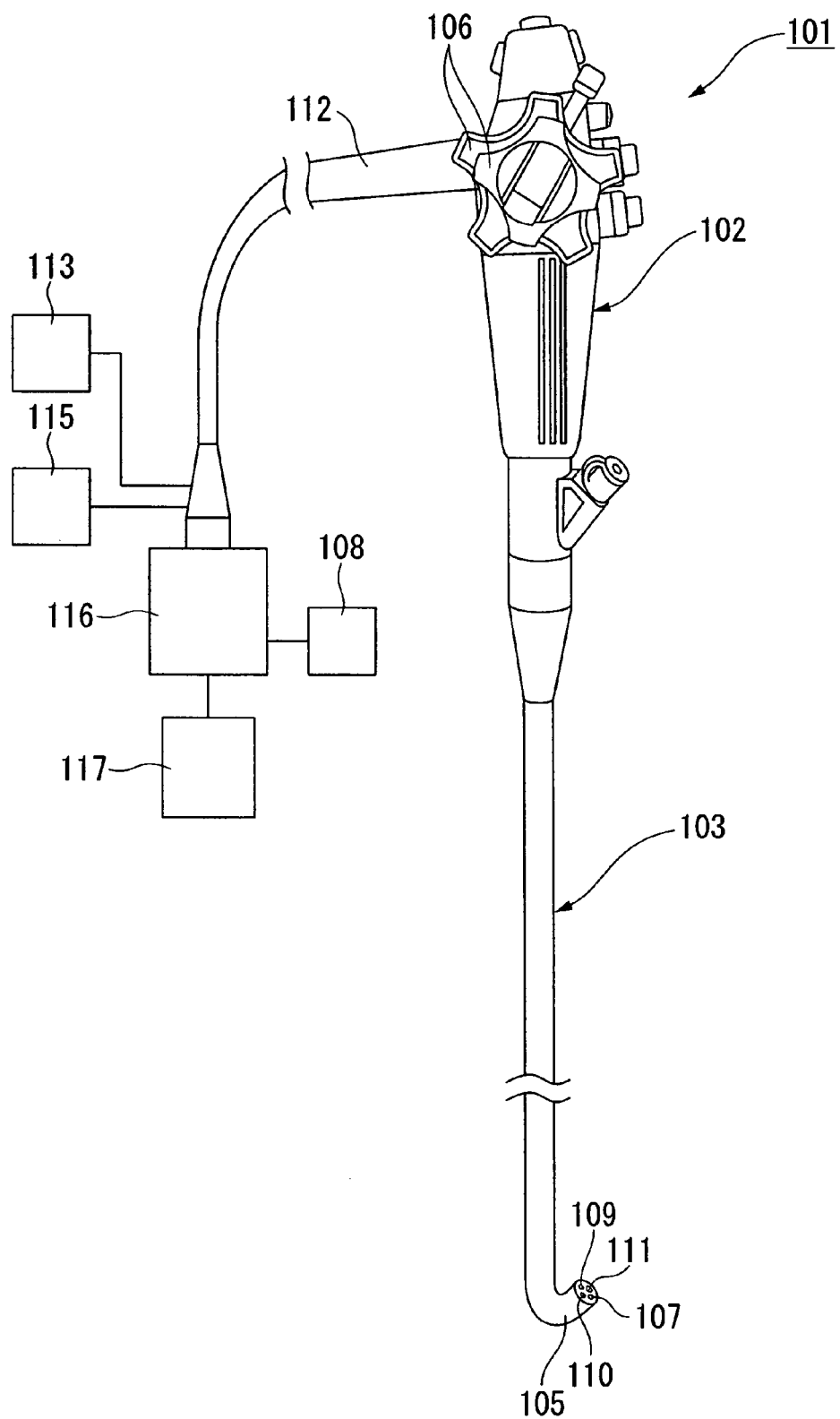
FIG. 18 is a view showing an endoscope employed in the seventh embodiment, as one example of a device used in a medical operation.

A flexible endoscope (referred to as "endoscope" hereinafter) 101 is shown in FIG. 18 as an example of a device employed in the present embodiment. The endoscope 101 is provided with an elongated insertion part 103 that extends out from an operation part 102, which is manipulated by the operator. An insertion part 103 has flexibility, and is inserted into the patient's body. The end 105 of the insertion part 103 can be bent by operating an angle knob 106 that is disposed to the operation part 102. An observation device (alternatively referred to as "observation device") 107, composed of an optical system for observation such as an objective lens or the like, and a CCD, used as an image pick-up element; an illuminating device 109 composed of an optical fiber for guiding light from a light source device 108 disposed outside the body, and an illuminating optical member for forming the light rays radiated from the end surface of the optical fiber into a desired form; and the end openings for channels 110 and 111; are disposed to the end of the insertion part 103. The channel 110 is a conduit that is connected to a gas/water supplying device 113 that is disposed outside the body, via a universal cable 112, and that is employed for supplying and evacuating liquid to and from the body. The channel 111 is a conduit that is attached to a suction device 115 or that is employed for inserting and removing instruments. The observed image that is input to the observation device 107 is displayed on a monitor 117 via a controller 116.

Figure 19:
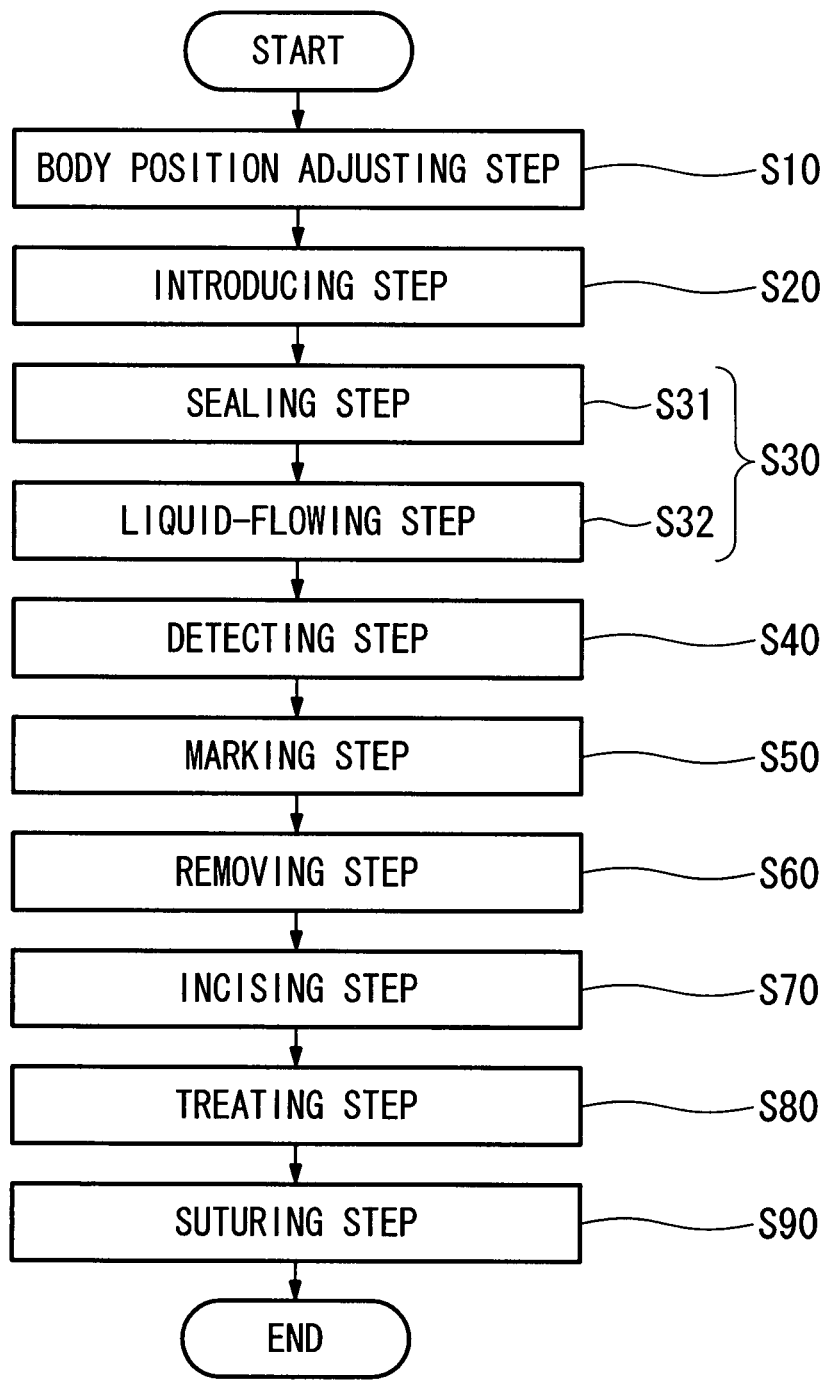
FIG. 19 is a flow diagram showing a medical operation according to the second embodiment.

The effects of the present embodiment in which this endoscope 101 is employed will be explained following the flow diagram shown in FIG. 19. Note that the following discussion explains a procedure in which the endoscope 101, which is an example of a procedure device for performing a specific procedure, is inserted via the mouth M of a patient PT into the stomach (hollow organ) ST, an opening is formed in the stomach wall, the insertion part 103 of the endoscope 101 is inserted into the abdominal cavity AC, and a procedure is performed. Note that in this case, the natural orifice into which the endoscope 101 is inserted is not limited to the mouth M; rather, this explanation is applicable to the nostrils, anus, or any other natural orifice. With regard to the medical operation carried out in the abdominal cavity AC, a variety of procedures, such as suturing, observation, incising, resection, cellular sampling, removal of a body organ or the like, may be carried out alone or in combination.

First, in body position adjusting step (S10), the body position of the patient PT is adjusted so that a target site T on the anterior wall of the stomach ST faces in the direction opposite the direction of gravitational force. In this embodiment, an arrangement is employed in which the patient PT is placed on his/her back, so that the anterior wall of the stomach ST, where the target site T is located, is directed upward.

Figure 20:
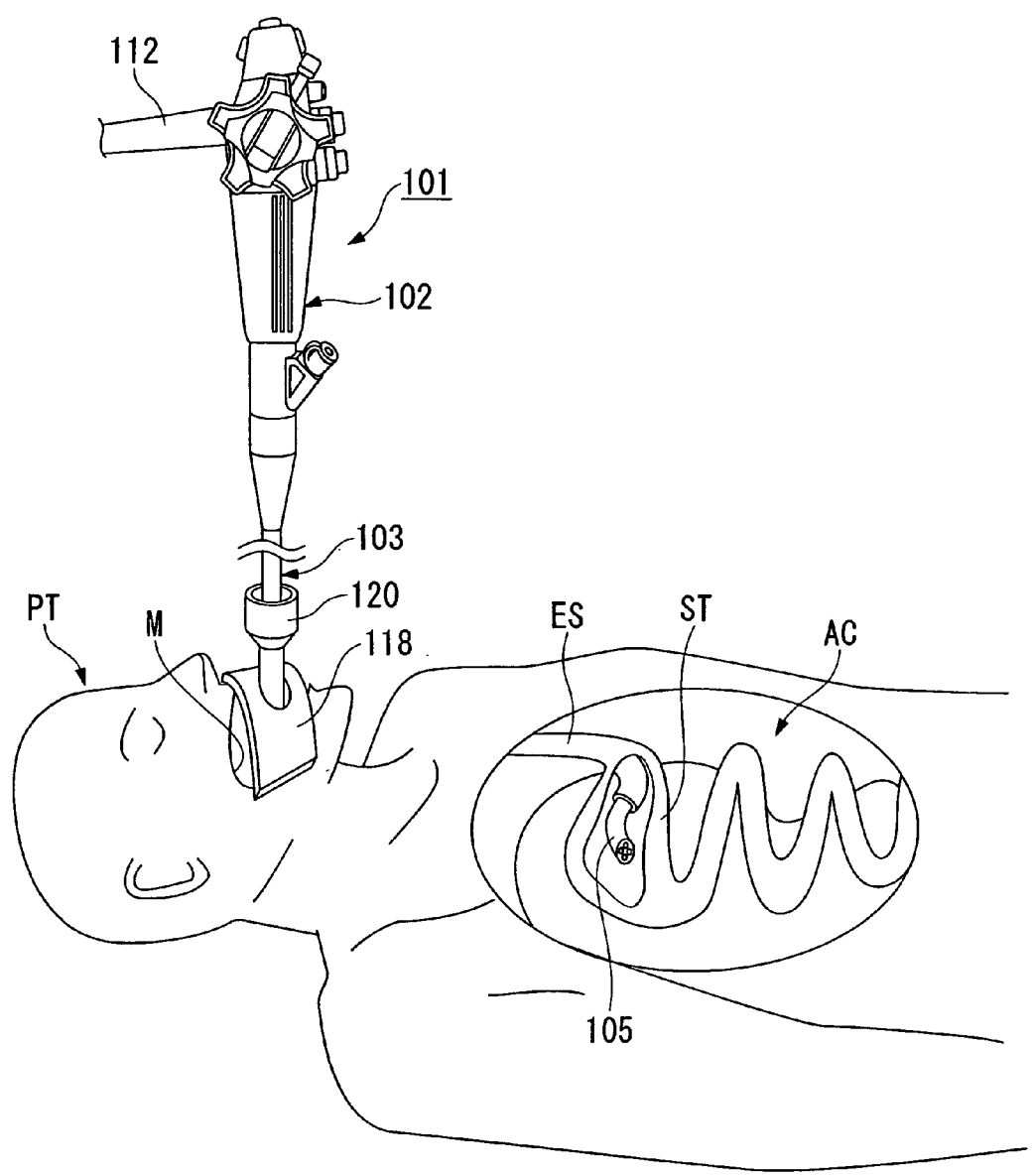
FIG. 20 is a view for explaining the arrangement for inserting the endoscope into the stomach, in a procedure according to the seventh embodiment.
Figure 21:
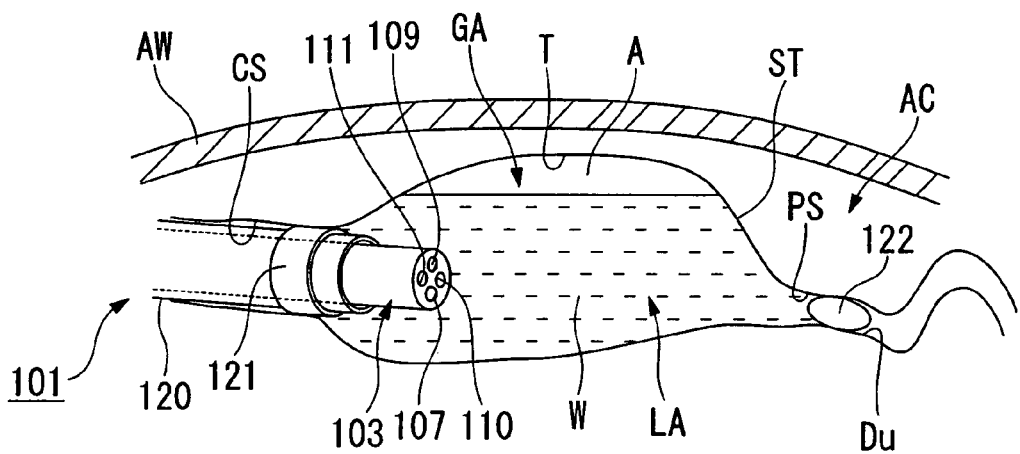
FIG. 21 is a view for explaining the arrangement for sending water by inserting an endoscope into the stomach, in a procedure according to the seventh embodiment.

Next, guiding step (S20), in which the endoscope 101 is inserted into the stomach ST, is carried out. Namely, a mouth piece 118 is attached at the mouth of the patient PT, and the endoscope 101 is inserted into the esophagus ES. It is preferable here to incorporate an overtube 120 during insertion of the endoscope into the body, as shown in FIG. 20. The overtube 120 is employed as a guide tube for inserting the endoscope 101 or another such device having an insertion part. However, it is also acceptable to directly insert the endoscope 1 without employing the overtube 120.

In the case where inserting the endoscope using the overtube 120, an attaching balloon (sealing member) 121 is attached at the distal end of the overtube 120. As shown in FIG. 20, the overtube 120 and the end of the insertion part 103 of the endoscope 101 are inserted into the stomach ST.

Next, the process proceeds to the area forming step (S30). A sealing step (S31) is first carried out in which the outlet side of the stomach ST (i.e., the forward direction of insertion of the endoscope) near the target site T (anterior wall of the stomach in this embodiment) is sealed. Specifically, an instrument is inserted into channel 111 of the endoscope 101, and a retaining balloon (sealing member) 122 is disposed in the duodenum Du in the forward direction of insertion of the endoscope 101. This retaining balloon 122 is then inflated in this position. The instrument is then removed, so that the retaining balloon 122 remains and seals the pylorus PS of the stomach ST. Sealing of the inlet side (i.e., the cardia CS side) of the stomach ST is then performed. Specifically, the attaching balloon 121 provided to the overtube 120 is inflated, sealing the space between the overtube 120 and the cardia CS. The space formed between the inner surface of the overtube 120 and the surface of a device such as the endoscope 101 that is inserted therein is sealed with a sealing member such as a valve, not shown in the figures, that is provided to the overtube 120. Note that, in this embodiment, both sides of the stomach ST (i.e., the one side and the other side of the hollow organ that have the area of the target site disposed therebetween) are sealed using sealing members such as attaching balloon 121 and the retaining balloon 122. However, it is also acceptable to omit sealing of the inlet side (i.e., the side into which the endoscope 101 or the overtube 120 is inserted) of the stomach ST. This is because in the case of the inlet side of the stomach ST, seal-tightness of the hollow organ can be assured to a certain degree by means of the inserted device such as the endoscope 101 or the overtube 120, as compared to the outlet side (i.e., the cardia CS side or the forward direction of insertion of the endoscope 101) of the stomach ST.

Figure 22:
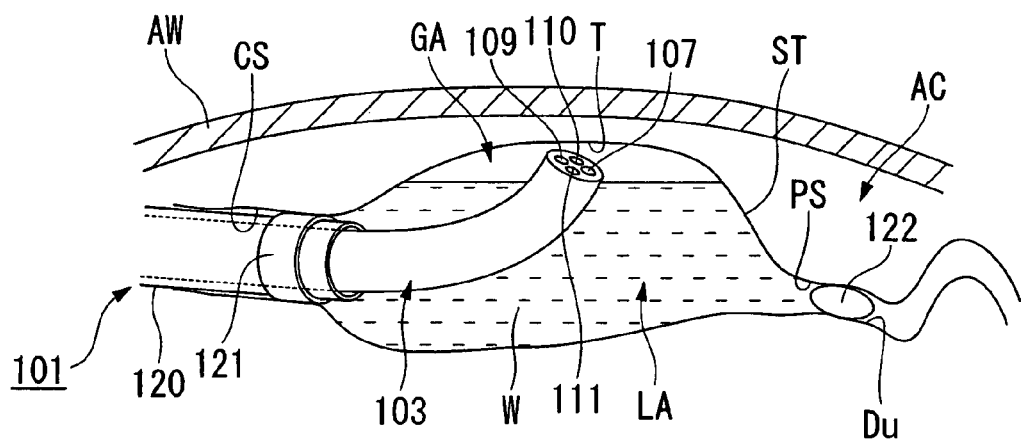
FIG. 22 is a view for explaining the arrangement in which the insertion part of the endoscope has been directed to the gas retaining area, in a procedure according to the seventh embodiment.

Next, the process proceeds to the liquid inflow step (S32). In this step, water is supplied into the stomach ST from channel 111 of the endoscope 101 which has been introduced into the stomach ST. Since both the cardia CS and the pylorus PS of the stomach ST are sealed at this time, water is held in the stomach ST as shown in FIG. 22. Since water W is heavier than air A, the water W supplied into the stomach ST is held in the bottom portion of the stomach ST, while air A rises to the top of the stomach ST. The target site T is positioned at the top of the stomach ST, where it is not dipped in water. In this way, a lower liquid holding area LA, and an upper gas retaining area GA, where gas remains and where the target site T is located, are formed.

Figure 23:
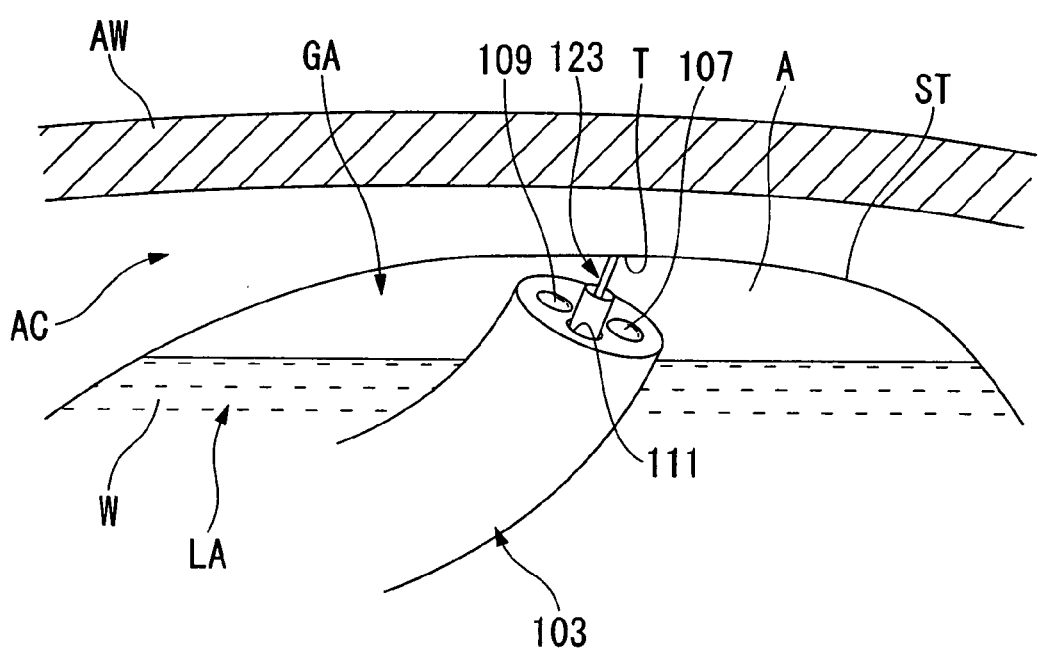
FIG. 23 is a view for explaining the arrangement for marking the target site, in a procedure according to the seventh embodiment.

The process then proceeds on to detecting step (S40). In this step, the angle knob 106 is operated to bend and manipulate the end of the insertion part 103 inside the stomach ST. The position of gas retaining area GA is confirmed during this operation, and the end of the insertion part 103 is moved from liquid holding area LA to gas retaining area GA. In this way, target incision site T is confirmed using the observation device 107, as shown in FIG. 23.

Figure 24:
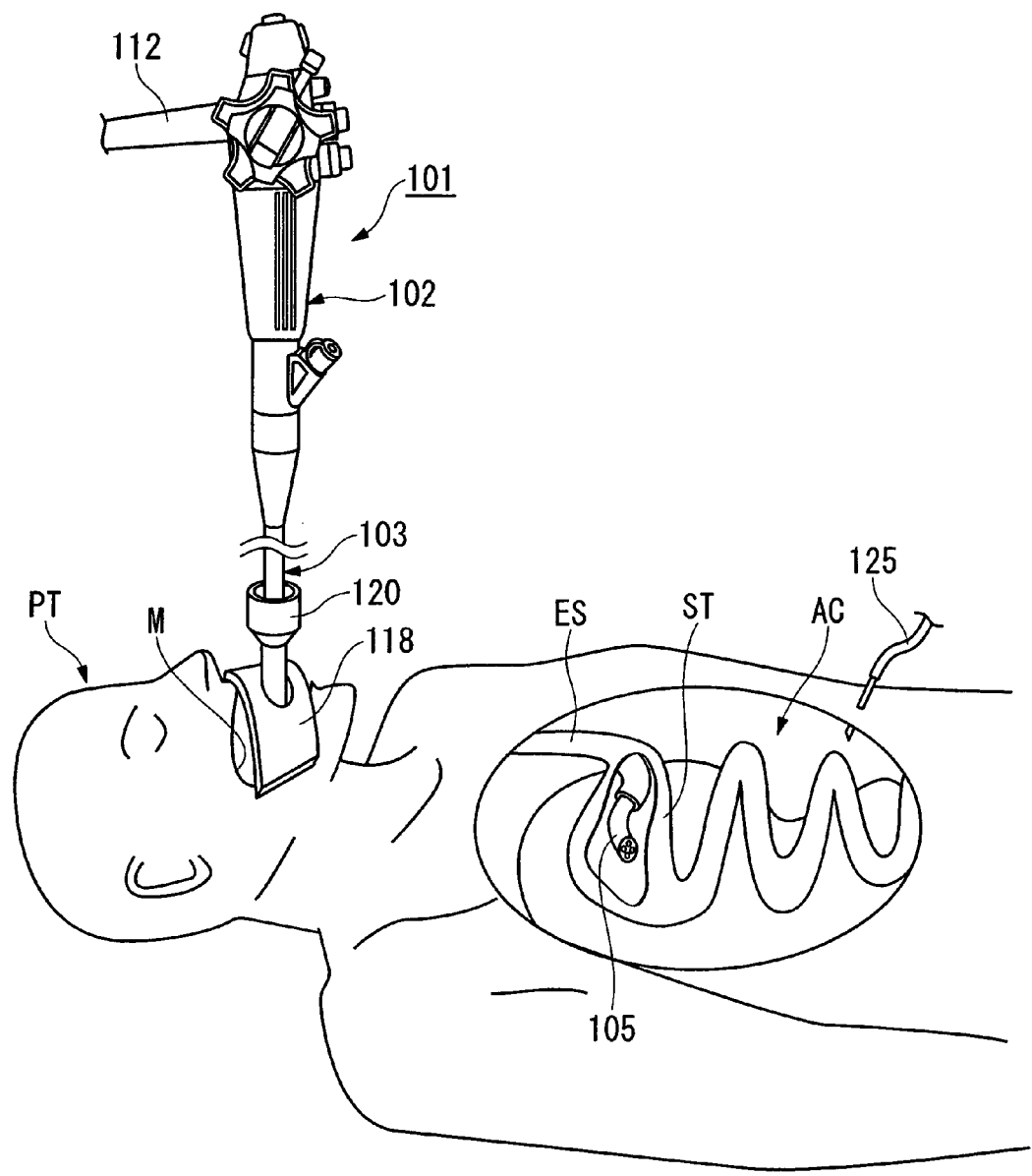
FIG. 24 is a view for explaining the arrangement for an insufflation, in a procedure according to the seventh embodiment.

Next, in marking step (S50), a the marking instrument 123 such as a high frequency knife, used for marking the stomach wall, is inserted into the channel 111 of the insertion part 103, and marking near the target site T is carried out as shown in FIG. 24. In order to prevent a short circuit, note that it is first confirmed that the area around the marking site is completely within gas retaining area GA. It is also acceptable to carry out this marking using a retained member, such as a clip or the like.

Once marking is completed, removing step (S60) is carried out. Namely, the marking instrument 123 is withdrawn from the channel 111, and the channel 111 and the suction device 113 are connected. The suction device 113 is then activated to remove the water W remaining in the stomach ST, expelling it to the outside of the body via the channel 111 of the endoscope 101.

Figure 25:
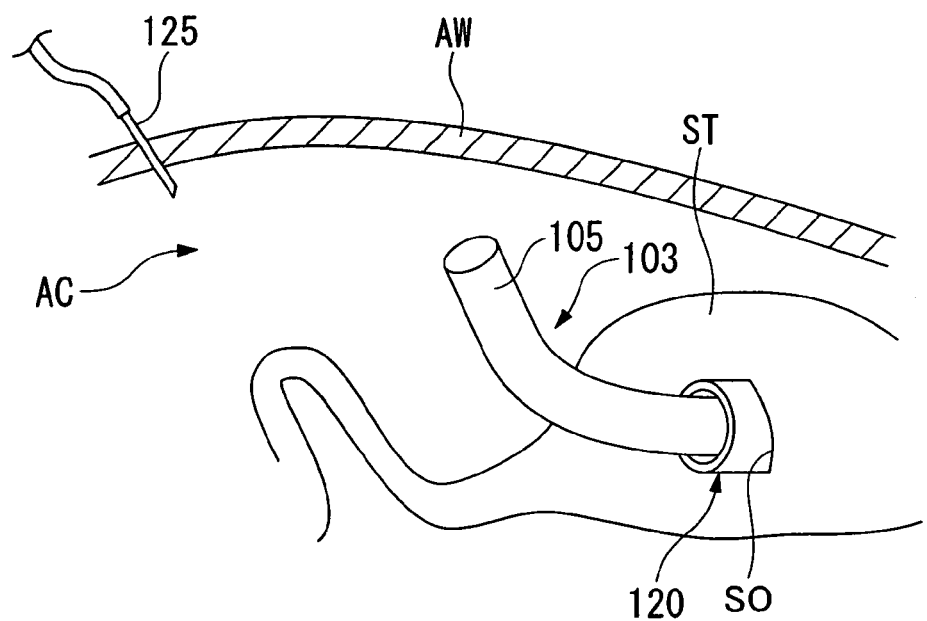
FIG. 25 is a view for explaining the state in which an opening has been incised in the stomach, in a procedure according to the seventh embodiment.

The process then proceeds to incising step (S70). The end of an insufflation needle (a conduit for supplying gas) 125 is passed from outside the body through an abdominal wall AW, and into the abdominal cavity AC, as shown in FIG. 25, for example. The abdominal cavity AC is then inflated with gas via the insufflation needle 125, to create a space between the stomach wall and the abdominal wall AW. In this embodiment, space between the stomach wall and the abdominal wall AW is secured by insufflating the abdominal cavity AC; however, it is not absolutely essential to carry out an insufflation step. Namely, it is also acceptable to employ conventionally known methods such as the suspension method to provide this space. In addition, it is also acceptable to perform the insufflating step in advance of the incising step. In addition, insufflation of the hollow organ is not absolutely required.

Next, the marking instrument 123 disposed inside the channel 111 is removed, and a high frequency knife for cutting is passed in its place through the channel 111 to extend out from the end opening. The marked target site T is then incised while observation the target site T on the monitor 117, to form an opening SO in the stomach wall (at a position corresponding to the target site T), the opening SO creating a communication between the inside of the stomach ST and the abdominal cavity AC. Note that a combined use instrument may be employed for the marking instrument and the instrument for forming the opening SO.

Figure 26:
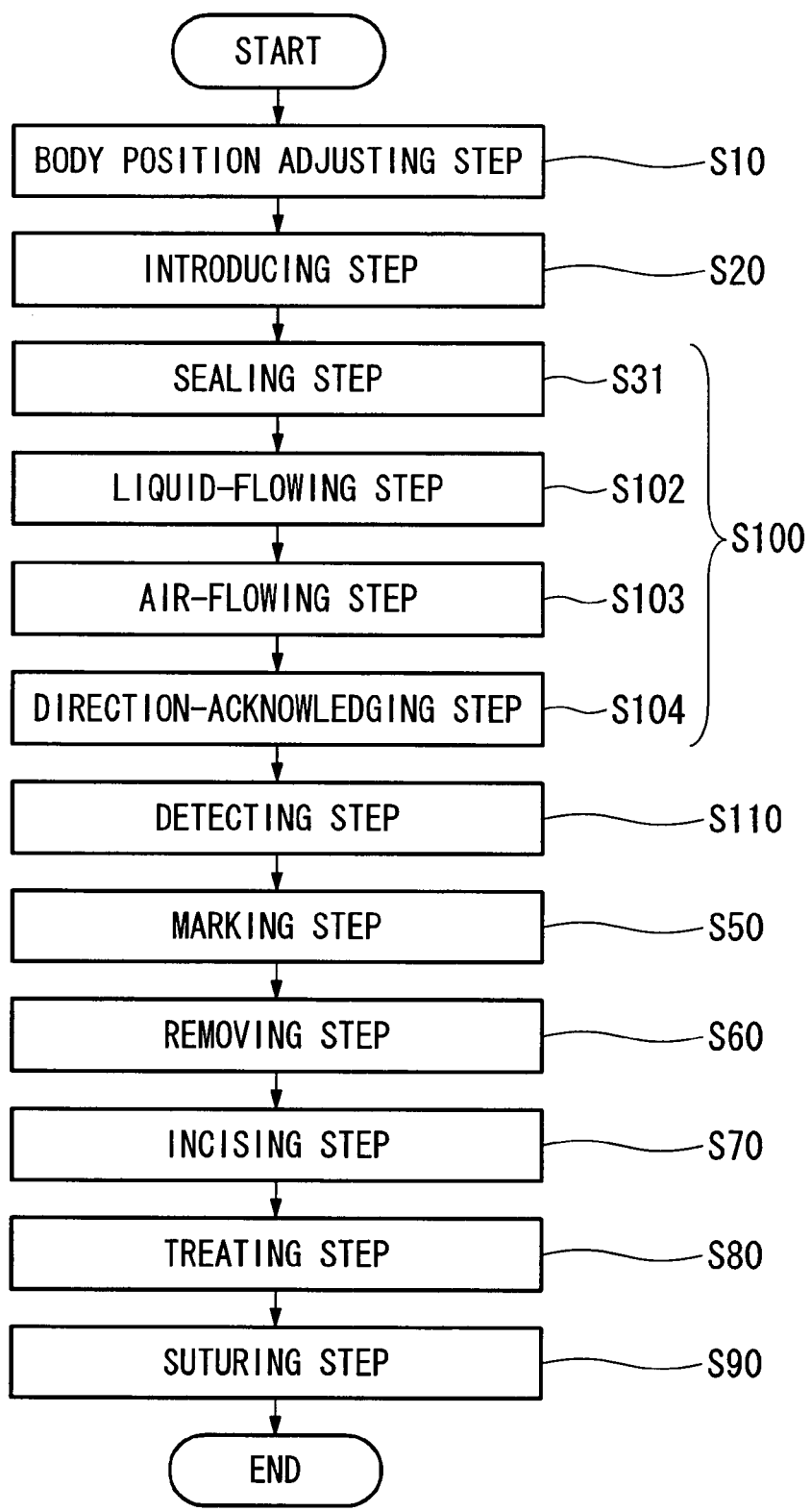
FIG. 26 is a flow diagram showing a medical operation according to the seventh embodiment.

After incising, as shown in FIG. 26, the end of the insertion part 103 is projected out into the abdominal cavity AC through the opening SO in the stomach wall, and procedure step (S80) is carried out in which various procedures such as suturing, observation, incising, resection, cell collection, organ removal or the like, are performed.

Next, the process proceeds to suturing step (S90), in which the opening SO in the stomach wall is sutured closed (the communicating path between the inside of the hollow organ and the abdominal cavity is closed) with a suturing instrument while using the observation device 107 of the endoscope 1 for confirmation.

After suturing, the endoscope 101 is withdrawn from the patient. In the case where the medical operation was performed by blowing carbon dioxide gas or the like into the abdominal cavity AC in order to secure space within the abdominal cavity, it is desirable to withdraw the insufflation needle 125 after first relieving the pressure within the abdominal cavity AC, and then conclude the medical operation.

In this embodiment, water was supplied into the stomach ST after positioning the patient PT so that the target site T is on top. As a result, by searching for the gas retaining area (GA) inside the stomach ST, it is possible to confirm the up/down direction from inside the stomach ST, and the target site T can be gripped. The stomach ST is sealed using attaching balloon 121 and the retaining balloon 122 during this operation. As a result, it is possible to grip the target site T by sending and expelling water to and from the stomach ST using the devices of a conventional endoscope 101, without requiring use of special equipment.

Since an incision is made in the anterior wall of the stomach ST, it is easy to avoid the greater omentum or other organs when introducing the endoscope into the abdominal cavity AC. As a result, the endoscope 101 can be readily inserted into the abdominal cavity AC, further facilitating the procedure.

In the past, it has been difficult to specify the direction or the location for a procedure (i.e. the location suitable for forming an opening) by means of the endoscope image alone, and practice was required for this procedure. However, in this embodiment, confirmation of the site is facilitated, reducing the burden on the operator.

In the seventh embodiment described above, the channel 110 is employed as a conduit for supplying water, and the channel 111 has a combined use as a conduit for inserting and passing instruments and as a conduit for expelling water. As another example, however, it is also acceptable to provide a combined use water supplying conduit and instrument inserting and passing conduit. In addition, a design is also acceptable in which the three functions of supplying water, expelling water, and instrument inserting/passing are accomplished by means of a single conduit. In addition, the hollow organ anterior and posterior to the target site were sealed using a sealing member, however, when it is possible to determine the direction of gravitational force and the direction opposite that using just a small amount of water, then it is not absolutely essential to carry out the sealing step.

[Eighth Embodiment]

An eighth embodiment will now be explained with reference to the figures.

The difference between the seventh and eighth embodiments is that, in this embodiment, the stomach ST is inflated with water, after which air is introduced into the stomach ST, and the target site T is searched for using the direction of movement of the air bubbles.

The effects of this embodiment will be explained following the flow shown in FIG. 26

First, the body position adjusting step (S10) and introducing step (S20) are carried out in the same manner as in the seventh embodiment. Namely, the position of the patient PT is adjusted so that the target site T is directed upward, and the overtube 120 and the endoscope 101 are inserted into the stomach ST.

Next, the process proceeds to area forming step (S100). First, sealing step (S31) is carried out, in which the retaining balloon 122 is retained in duodenum Du. In this way, the pylorus PS of the stomach ST and the cardia CS of the stomach ST are sealed.

Figure 27:
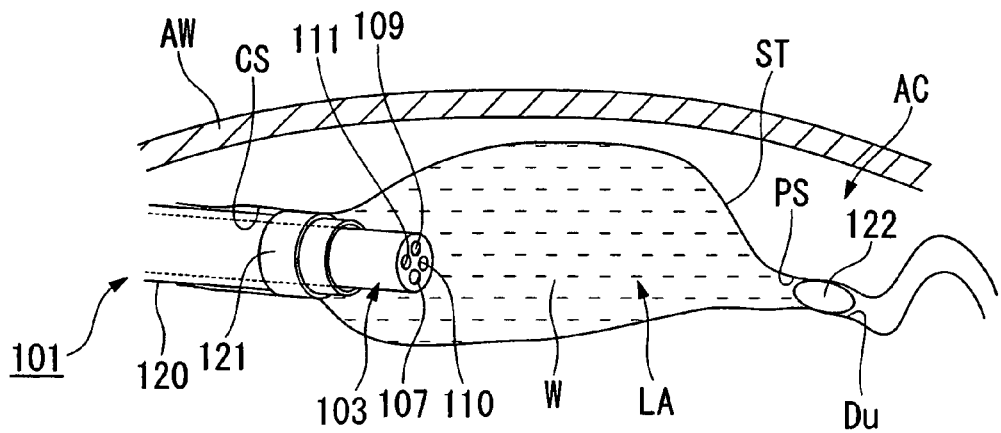
FIG. 27 is a view for explaining the arrangement in which water is supplied into the stomach to inflate it, in a procedure according to an eighth embodiment.
Figure 28:
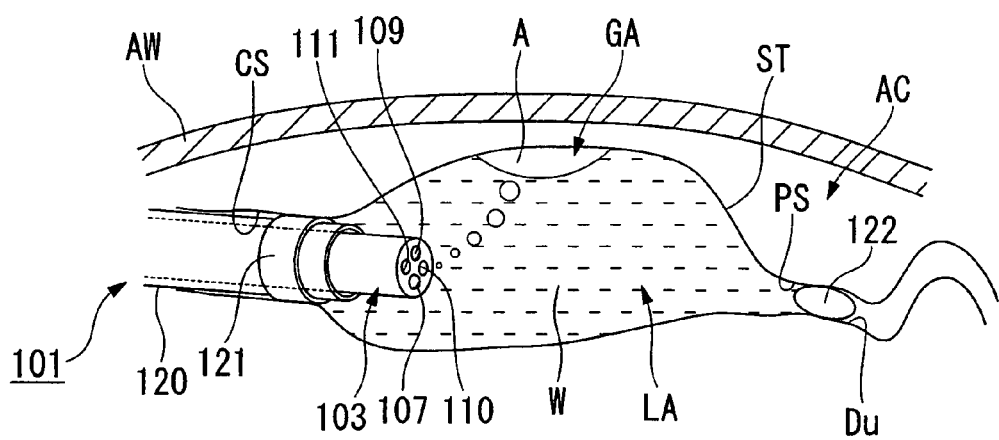
FIG. 28 is a view for explaining the arrangement for confirming the direction of movement of bubbles using the insertion part of the endoscope, in a procedure according to the eighth embodiment.

Next, the process proceeds to liquid inflow step (S102). As shown in FIG. 27, water is supplied into the stomach ST via the channel 111 of the endoscope 101 which has been inserted into the stomach ST, inflating the stomach ST with water W. Once the stomach ST is inflated, the process proceeds to gas inflow step (S103). Namely, air A is introduced into the stomach ST from an air/water supplying device 113 via the channel 110 of the endoscope 101. Since air A is lighter than water W, the air A introduced into the stomach ST forms bubbles B and moves through water W to the top of the stomach ST, as shown in FIG. 28. In this way, a liquid holding area LA is formed at the bottom and a gas retaining area GA, where the air remains, is formed at the top within the stomach ST.

Direction recognition step (S104) is executed almost simultaneously. Namely, the movement behavior of bubbles B from air A expelled from the end of the insertion part 103 of the endoscope 101 in gas inflow step (S103) is observed, thereby allowing determination of the up/down direction within the stomach ST (alternatively, the up/down direction in the stomach ST may be determined by determining the direction where gas retaining area GA is formed).

The process then proceeds on to detecting step (S110). The end of the insertion part 103 is moved from liquid holding area LA to gas retaining area GA while being bent and manipulated by operating the angle knob 106.

Subsequently, the marking step (S50), removing step (S60), incising step (S70), procedure step (S80), and suturing step (S90) are each executed in the same manner as in the seventh embodiment. After suturing is completed, the endoscope 101 is removed from the patient, the insufflation needle 125 is removed after relieving the pressure inside the abdominal cavity AC, and the procedure is terminated.

In this embodiment, the up/down direction in the stomach ST was determined by observing bubbles B moving through water W. As a result, gas retaining area GA can be recognized more easily than in the first embodiment, and searching for the target site T is facilitated. Note that in the second embodiment, the channel 111 is used as a water supplying conduit and the channel 110 is used as a gas supplying conduit. However, as a separate example, a design is also acceptable in which the water supplying conduit and the gas supplying conduit are accomplished as single conduits. Alternatively, it is also acceptable to provide combined use of water supplying conduit and gas supplying conduit. In addition, a design may also be employed in which all the functions are carried out through a single conduit.

The technical scope of the present invention is not limited to the embodiments described above. Rather, various modifications may be added provided that they do not depart from the spirit of the invention.

For example, the stomach was employed as an example of a hollow organ in the above embodiments. However, the present invention is not limited thereto; rather, the present invention may be used with other hollow organs into which an endoscope can be inserted via a natural orifice. In addition, while water was supplied into the stomach ST in the above embodiments, it is also acceptable to supply a liquid medication. When an antibacterial agent is used as the medication, then it is possible to carry out the procedure in combination with disinfecting the stomach ST to remove such bacteria as *Helicobacter pylori*. It is also acceptable to use an antibiotic as the liquid medication. Further, the sequence for the various steps of the medical operation is not limited to that disclosed in the preceding embodiments; any sequence is permissible, provided that it allows liquid to be supplied into the hollow organ. The same procedure may also be carried out while observation the inside of the body using an observation device of the type that wirelessly sends images taken up by a conventionally known capsule endoscope or other such equipment that is retained inside the body, or a wireless type observation device that uses a device (i.e., device for performing a procedure) having an insertion part that does not have a observation function.

The above embodiments showed a medical operation using an overtube; however, it is also acceptable to insert the endoscope into the body without using the overtube. In this case, it is possible to provide an attaching balloon identical to that of the embodiments, to the insertion part of the endoscope, to seal the space between the insertion part and the hollow organ.

What is claimed is:

1. A medical retainer for sealing a fluid, the retainer being retained in a gastrointestinal tract of a patient, the medical retainer comprising:

a sealing section for sealing the fluid, the sealing section making contact with a wall of the gastrointestinal tract;
a main body having a passageway, one portion of the main body being surrounded by the sealing section;
a first one-way valve disposed in the passageway for allowing flow of the fluid only from downstream to upstream in an insertion direction of the retainer; and
a first tube for suctioning the fluid accumulated in a downstream portion of the gastrointestinal tract with respect to a detained position of the retainer, wherein
the first tube is detachably connected through the first one-way valve to the passageway;
the first tube is inserted through an upstream portion of the gastrointestinal tract;
the first tube is communicated between the downstream portion of the gastrointestinal tract and an exterior of the patient;
the main body has an upstream surface facing an upward portion of the gastrointestinal tract and a downstream surface facing a downward portion of the gastrointestinal tract; and
the first one-way valve is formed on the upstream surface of the passageway.

2. The medical retainer according to claim 1, wherein the gastrointestinal tract is a duodenum.

3. The medical retainer according to claim 1, further comprising a connection structure wherein the first tube connected to the first one-way valve releases the upstream portion of the gastrointestinal tract to the downstream portion of the gastrointestinal tract.

4. The medical retainer according to claim 1, wherein the first tube is introduced to the exterior of the patient so that the downstream portion of the gastrointestinal tract can be released to an ambient pressure.

5. The medical retainer according to claim 1, wherein
the sealing section is an expandable balloon,
the main body has a connection port on the upstream surface of the main body, the connection port being connected to a second tube for supplying air for inflating the balloon, and
the second tube has a second one-way valve.

6. The medical retainer according to claim 1, wherein
the main body has an outer circumference, and
the sealing section is disposed on the outer circumference.

7. The medical retainer according to claim 1, wherein the sealing section is an expandable member making contact with the wall of the gastrintestinal tract to seal the fluid.

8. A natural orifice medical operation using a medical retainer for sealing a fluid, the retainer being retained in a duodenum of a patient, the medical retainer comprising:
a sealing section for sealing the fluid, the sealing section making contact with a wall of the duodenum;
a main body having a passageway, one portion of the main body being surrounded by the sealing section;
a first one-way valve disposed in the passageway for allowing flow of the fluid only from downstream to upstream in an insertion direction of the retainer;
a first tube for suctioning the fluid accumulated in a downstream portion of the gastrointestinal tract with respect to a detained position of the retainer, wherein
the first tube is detachably connected through the first one-way valve to the passageway, the first tube is inserted through an upstream portion of the gastrointestinal tract;
the first tube is communicated between the downstream portion of the gastrointestinal tract and an exterior of a patient;
the main body has an upstream surface facing an upward portion of the gastrointestinal tract and a downstream surface facing a downward portion of the gastrointestinal tract; and
the first one-way valve is formed on the upstream surface of the passageway,
the operation comprising:
inserting the medical retainer into the duodenum of a patient by using an endoscopic device;
retaining the medical retainer in the duodenum;
conducting a medical treatment on the patient; and
collecting the medical retainer from the inside of the patient to the exterior of the patient.

9. The medical operation according to claim 8, wherein the medical treatment includes adjusting the gas pressure in the downward portion of the gastrointestinal tract of the patient.

10. The medical operation according to claim 8, wherein the medical treatment includes releasing the downstream portion of the gastrointestinal tract of the patient to an ambient.

11. The medical operation according to claim 8, wherein the medical treatment includes releasing the downstream portion of the gastrointestinal tract of the patient to an inner pressure of a stomach.

12. The medical operation according to claim 8, wherein collecting the medical retainer from the inside to outside of the patient includes contracting the medical retainer.

13. The medical operation according to claim 8, wherein the medical treatment includes supplying air into a stomach of the patient.

14. The medical operation according to claim 8, wherein the operation is gastrically conducted in the abdominal cavity.

15. The medical operation according to claim 14, further comprising:
retaining in the duodenum;
incising an intended site of a wall of a stomach by using an endoscopic device; and
conducting a medical treatment in an abdominal cavity.

* * * * *